United States Patent
Py

(10) Patent No.: US 10,426,701 B2
(45) Date of Patent: Oct. 1, 2019

(54) SINGLE USE CONNECTORS

(71) Applicant: Daniel Py, Larchmont, NY (US)

(72) Inventor: Daniel Py, Larchmont, NY (US)

(73) Assignee: MEDINSTILL DEVELOPMENT LLC, New Milford, CT (US)

( * ) Notice: Subject to any disclaimer, the term of this patent is extended or adjusted under 35 U.S.C. 154(b) by 72 days.

(21) Appl. No.: 15/410,762

(22) Filed: Jan. 19, 2017

(65) Prior Publication Data
US 2017/0202741 A1   Jul. 20, 2017

Related U.S. Application Data

(60) Provisional application No. 62/280,693, filed on Jan. 19, 2016.

(51) Int. Cl.
| | |
|---|---|
| *A61J 1/20* | (2006.01) |
| *A61M 5/162* | (2006.01) |
| *A61M 39/10* | (2006.01) |
| *A61M 39/18* | (2006.01) |
| *A61M 39/26* | (2006.01) |

(52) U.S. Cl.
CPC ............. *A61J 1/201* (2015.05); *A61J 1/2055* (2015.05); *A61M 5/162* (2013.01); *A61M 5/1626* (2013.01); *A61M 39/10* (2013.01); *A61M 39/1011* (2013.01); *A61M 39/18* (2013.01); *A61M 2039/267* (2013.01)

(58) Field of Classification Search
CPC .. A61J 1/20; A61J 1/201; A61J 1/2055; A61J 1/2024; A61J 1/2031; A61M 39/1011; A61M 39/1066; A61M 39/165; B65B 3/003
See application file for complete search history.

(56) References Cited

U.S. PATENT DOCUMENTS

| | | | |
|---|---|---|---|
| 2,304,390 A | 12/1942 | Wolfram | |
| 2,819,914 A | 1/1958 | Eitner | |
| 3,367,366 A | 2/1968 | Oliveau et al. | |
| (Continued) | | | |

FOREIGN PATENT DOCUMENTS

| | | |
|---|---|---|
| CN | 1755181 A | 4/2006 |
| EP | 0043698 B1 | 10/1984 |
| (Continued) | | |

OTHER PUBLICATIONS

International Search Report and Written Opinion issued in International Application No. PCT/US2017/014204 dated May 24, 2017. 10 Pages.

*Primary Examiner* — Nicolas A Arnett
(74) *Attorney, Agent, or Firm* — McCarter & English, LLP

(57) ABSTRACT

Connector assembly including a piercing member having a flow port therein attached to a first piece, with the piercing member slidingly receivable within a second piece, wherein the piercing member and the second pierce are movable relative to each other between a first position where the second pieces closes the flow port and a second position where the flow port is open. The first piece contains a locking mechanism that lockingly engages with a device when connected thereto, preventing subsequent disconnection of first piece and the device. Upon initial connection of the first piece to the device, the second piece is moved from the first position to the second position.

27 Claims, 19 Drawing Sheets

(56) References Cited

U.S. PATENT DOCUMENTS

| | | |
|---|---|---|
| 3,406,872 A | 10/1968 | Fiquet et al. |
| 3,777,771 A | 12/1973 | De Visscher |
| 3,916,929 A | 11/1975 | Brown |
| 4,076,147 A | 2/1978 | Schmit |
| 4,112,944 A | 9/1978 | Williams |
| 4,232,851 A | 11/1980 | Johnson |
| 4,384,660 A | 5/1983 | Palmisano et al. |
| 4,421,146 A | 12/1983 | Bond et al. |
| 4,440,316 A | 4/1984 | Christine |
| 4,473,369 A | 9/1984 | Lueders et al. |
| 4,610,469 A | 9/1986 | Wolff-Mooij |
| 4,700,744 A | 10/1987 | Rutter et al. |
| 4,706,827 A | 11/1987 | Cabernoch et al. |
| 4,709,725 A | 12/1987 | Morrison |
| 4,752,292 A | 6/1988 | Lopez et al. |
| 4,778,453 A | 10/1988 | Lopez |
| 4,790,832 A | 12/1988 | Lopez |
| 4,798,605 A | 1/1989 | Steiner et al. |
| 4,804,015 A | 2/1989 | Albinsson |
| 4,816,024 A | 3/1989 | Sitar et al. |
| 4,842,591 A | 6/1989 | Luther |
| 4,846,805 A | 7/1989 | Sitar |
| 4,917,149 A | 4/1990 | Grantham |
| 4,931,048 A | 6/1990 | Lopez |
| 4,941,517 A | 7/1990 | Galloway |
| 4,946,040 A | 8/1990 | Ipenburg |
| 5,127,550 A | 7/1992 | Knorr |
| 5,199,947 A | 4/1993 | Lopez et al. |
| 5,211,197 A | 5/1993 | Marrison et al. |
| 5,281,206 A | 1/1994 | Lopez |
| 5,344,414 A | 9/1994 | Lopez et al. |
| 5,352,210 A | 10/1994 | Marrucchi |
| 5,474,209 A | 12/1995 | Vallet Mas et al. |
| 5,478,328 A | 12/1995 | Silverman et al. |
| 5,482,083 A | 1/1996 | Jenski |
| 5,492,147 A | 2/1996 | Challender et al. |
| 5,501,676 A * | 3/1996 | Niedospial ............ A61J 1/2096 604/403 |
| 5,694,686 A | 12/1997 | Lopez et al. |
| 5,791,376 A | 8/1998 | Richmond |
| 5,810,768 A | 9/1998 | Lopez |
| 5,810,792 A | 9/1998 | Fangrow, Jr. et al. |
| 6,024,242 A | 2/2000 | Stevenson |
| 6,032,691 A | 3/2000 | Powell et al. |
| 6,039,302 A | 3/2000 | Cote et al. |
| 6,041,805 A | 3/2000 | Gydesen et al. |
| 6,079,444 A | 6/2000 | Harris et al. |
| 6,082,584 A | 7/2000 | Stern |
| 6,082,585 A | 7/2000 | Mader et al. |
| 6,109,315 A | 8/2000 | Stern |
| 6,135,150 A | 10/2000 | Powell et al. |
| 6,245,048 B1 | 6/2001 | Fangrow, Jr. et al. |
| 6,428,520 B1 | 8/2002 | Lopez et al. |
| 6,582,415 B1 * | 6/2003 | Fowles ................ A61J 1/1406 137/614.04 |
| 6,599,273 B1 | 7/2003 | Lopez |
| 6,604,561 B2 | 8/2003 | Py |
| 6,634,384 B2 | 10/2003 | Skeens et al. |
| 6,651,955 B2 | 11/2003 | Anderson |
| 6,655,655 B1 | 12/2003 | Matkovich et al. |
| 6,659,994 B1 | 12/2003 | Mader et al. |
| 6,679,529 B2 | 1/2004 | Johnson et al. |
| 6,685,674 B2 | 2/2004 | Douglas et al. |
| 6,695,817 B1 | 2/2004 | Fangrow, Jr. |
| 6,726,672 B1 | 4/2004 | Hanly et al. |
| 6,772,911 B2 | 8/2004 | Gee et al. |
| 6,866,158 B1 | 3/2005 | Sommer et al. |
| 6,880,801 B2 | 4/2005 | Matkovich et al. |
| 6,890,328 B2 * | 5/2005 | Fowles .................... A61J 1/10 604/413 |
| 6,892,760 B2 | 5/2005 | Roos et al. |
| 6,837,878 B2 | 6/2005 | Smutney et al. |
| 6,916,309 B2 | 7/2005 | Fangrow |
| 7,032,631 B2 | 4/2006 | Py |
| 7,077,176 B2 | 7/2006 | Py |
| 7,090,191 B2 | 8/2006 | Matkovich et al. |
| 7,099,731 B2 | 8/2006 | Lopez |
| 7,100,646 B2 | 9/2006 | Py et al. |
| 7,137,974 B2 | 11/2006 | Almasian et al. |
| 7,156,826 B2 | 1/2007 | Ishii et al. |
| 7,174,914 B2 | 2/2007 | Ooishi et al. |
| 7,309,326 B2 | 12/2007 | Fangrow, Jr. |
| 7,354,427 B2 | 4/2008 | Fangrow |
| 7,396,348 B2 | 7/2008 | Newton et al. |
| 7,425,209 B2 * | 9/2008 | Fowles ................ A61J 1/1406 604/403 |
| 7,507,227 B2 | 3/2009 | Fangrow |
| 7,510,547 B2 | 3/2009 | Fangrow |
| 7,510,548 B2 | 3/2009 | Fangrow |
| 7,513,895 B2 | 4/2009 | Fangrow |
| 7,523,918 B2 | 4/2009 | Matkovich et al. |
| 7,534,239 B1 | 5/2009 | Fangrow |
| 7,547,300 B2 | 6/2009 | Fangrow |
| 7,568,509 B2 | 8/2009 | Py |
| 7,569,043 B2 | 8/2009 | Fangrow |
| 7,645,271 B2 | 1/2010 | Fangrow |
| 7,654,995 B2 | 2/2010 | Warren et al. |
| 7,658,205 B1 | 2/2010 | Edelman et al. |
| 7,658,733 B2 | 2/2010 | Fangrow |
| 7,670,322 B2 | 3/2010 | Fangrow, Jr. |
| 7,713,250 B2 | 5/2010 | Harding et al. |
| 7,758,566 B2 | 7/2010 | Simpson et al. |
| 7,779,609 B2 | 8/2010 | Py |
| 7,803,139 B2 | 9/2010 | Fangrow, Jr. |
| 7,824,393 B2 | 11/2010 | Fangrow |
| 7,883,499 B2 | 2/2011 | Fangrow |
| 7,892,216 B2 | 2/2011 | Fangrow, Jr. |
| 7,921,875 B2 | 4/2011 | Moriiki et al. |
| 7,931,615 B2 | 4/2011 | Fangrow, Jr. |
| 8,105,314 B2 | 1/2012 | Fangrow, Jr. |
| 8,196,606 B2 | 6/2012 | Kitagawa |
| 8,409,164 B2 | 4/2013 | Fangrow |
| 8,454,579 B2 | 6/2013 | Fangrow, Jr. |
| 8,522,832 B2 | 9/2013 | Lopez et al. |
| 8,552,832 B2 | 10/2013 | Kohanek |
| 8,602,246 B2 | 12/2013 | Frohwein |
| 8,647,310 B2 | 2/2014 | Fangrow, Jr. et al. |
| 8,758,306 B2 | 6/2014 | Lopez et al. |
| 8,759,306 B2 | 6/2014 | Lopez et al. |
| 8,956,330 B2 | 2/2015 | Fangrow, Jr. |
| 2002/0188260 A1 | 12/2002 | Gollobin |
| 2002/0189712 A1 | 12/2002 | Safabash |
| 2003/0032940 A1 | 2/2003 | Doyle |
| 2003/0106610 A1 | 2/2003 | Roos et al. |
| 2004/0124389 A1 | 12/2004 | Phillips |
| 2004/0256026 A1 | 12/2004 | Py |
| 2006/0142735 A1 | 6/2006 | Whitley |
| 2006/0287639 A1 | 12/2006 | Sharp |
| 2007/0095857 A1 | 5/2007 | Py et al. |
| 2007/0106225 A1 | 5/2007 | Millerd |
| 2007/0225635 A1 | 9/2007 | Lynn |
| 2008/0048436 A1 | 2/2008 | Matkovich et al. |
| 2008/0185056 A1 | 8/2008 | Diodati et al. |
| 2008/0197626 A1 | 8/2008 | Coambs et al. |
| 2008/0223484 A1 | 9/2008 | Horppu |
| 2009/0008417 A1 | 1/2009 | Gunn |
| 2009/0050213 A1 | 2/2009 | Biddell |
| 2009/0139949 A1 | 6/2009 | Py et al. |
| 2009/0179547 A1 | 7/2009 | Auday et al. |
| 2009/0232586 A1 | 9/2009 | Diodati et al. |
| 2009/0243281 A1 | 10/2009 | Seifert et al. |
| 2009/0292274 A1 | 11/2009 | Guala |
| 2010/0007134 A1 | 1/2010 | Elton et al. |
| 2010/0021230 A1 | 1/2010 | Olivier |
| 2010/0108681 A1 | 5/2010 | Jepson et al. |
| 2010/0140290 A1 | 6/2010 | Py |
| 2011/0060312 A1 | 3/2011 | Scheurer |
| 2011/0186764 A1 | 8/2011 | Takami |
| 2011/0240158 A1 | 10/2011 | Py |
| 2012/0042971 A1 | 2/2012 | Py |
| 2012/0097705 A1 | 4/2012 | Py |
| 2012/0118416 A1 | 5/2012 | Johnson |
| 2012/0261027 A1 | 10/2012 | Py |
| 2013/0270820 A1 | 10/2013 | Py et al. |

(56) References Cited

U.S. PATENT DOCUMENTS

| | | |
|---|---|---|
| 2013/0292592 A1 | 11/2013 | Py |
| 2014/0288528 A1 | 9/2014 | Py |
| 2015/0122369 A1 | 5/2015 | Py |
| 2015/0321780 A1 | 11/2015 | Py |
| 2016/0213910 A1 | 7/2016 | Fangrow |

FOREIGN PATENT DOCUMENTS

| | | |
|---|---|---|
| EP | 1260245 | 11/2002 |
| EP | 0981389 B1 | 12/2003 |
| EP | 1297861 B1 | 9/2006 |
| EP | 1716885 | 11/2006 |
| EP | 2042798 A1 | 4/2009 |
| EP | 2298407 A1 | 3/2011 |
| FR | 2699522 B1 | 1/1995 |
| WO | 93/11828 | 6/1993 |
| WO | 0198158 A1 | 12/2001 |
| WO | 2009035383 A1 | 3/2009 |
| WO | 2011117283 A2 | 9/2011 |

* cited by examiner

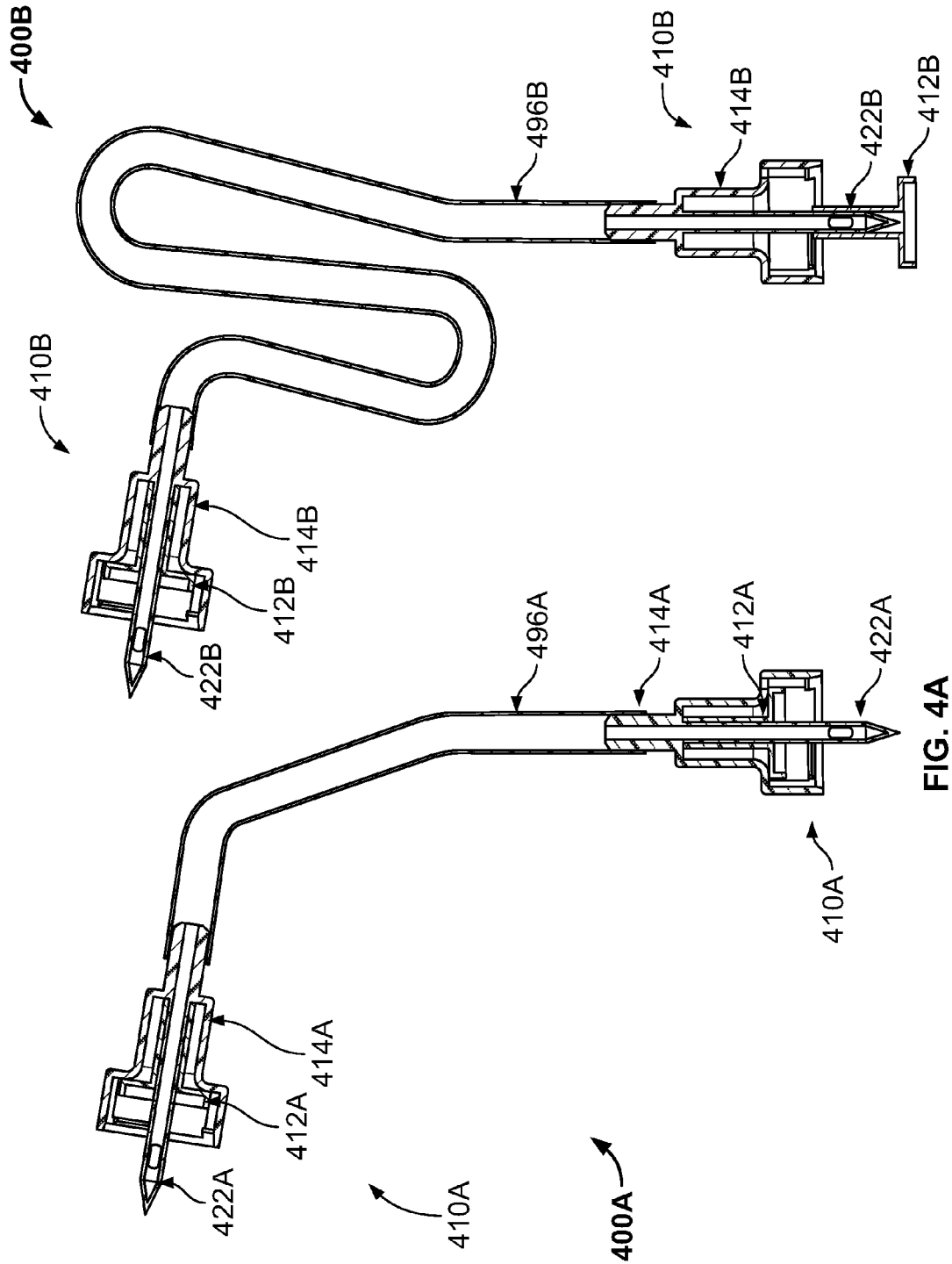

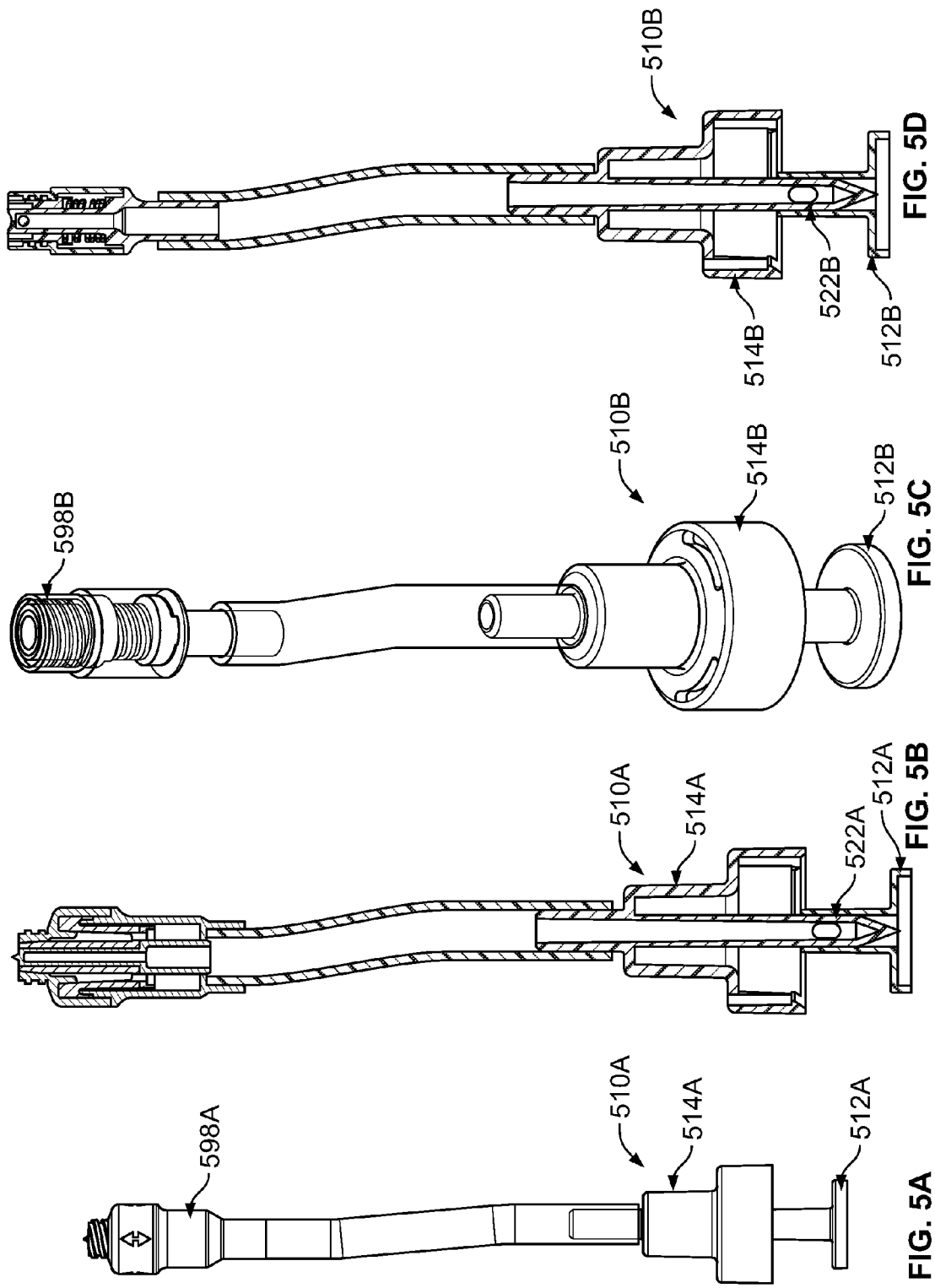

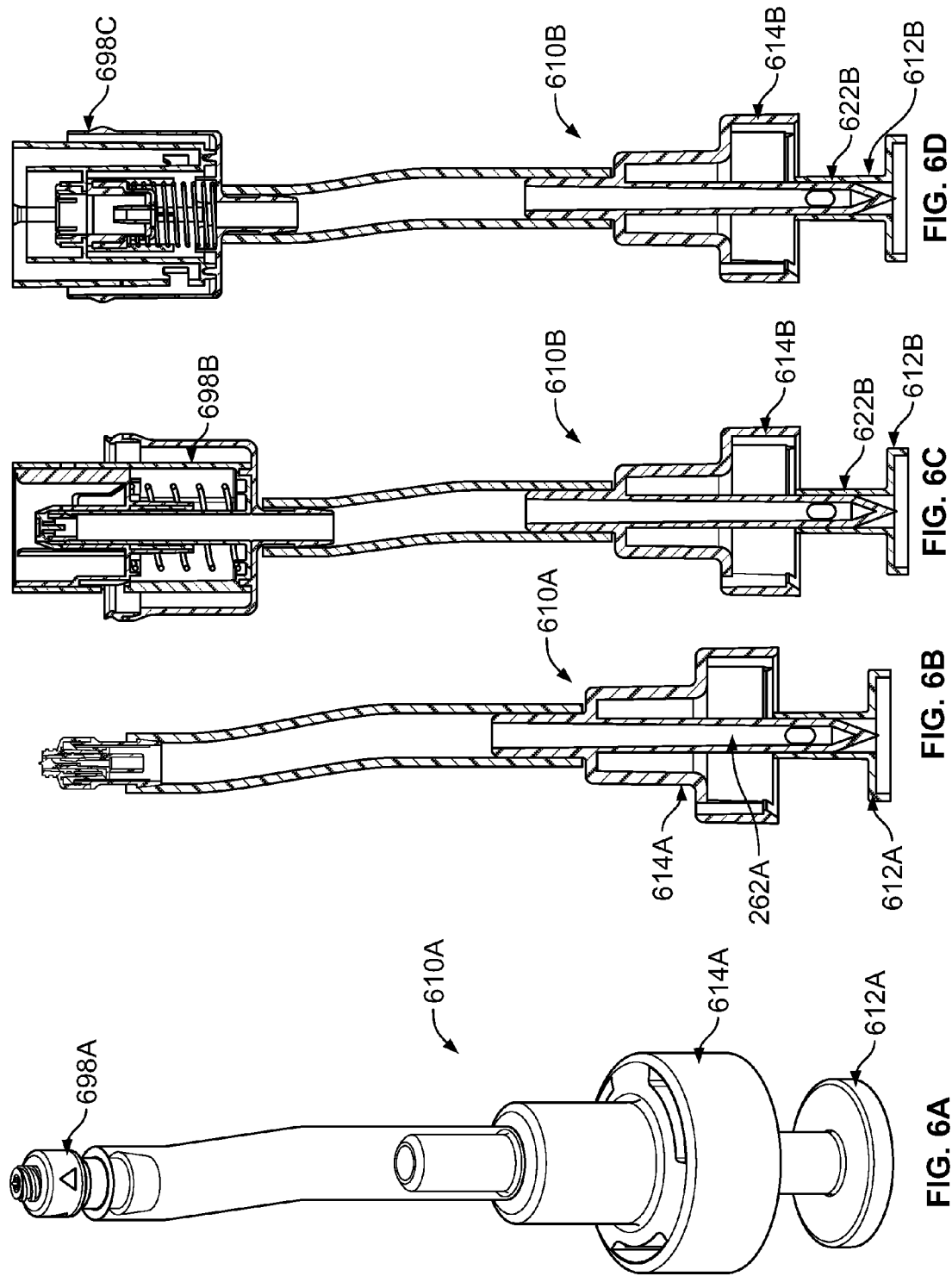

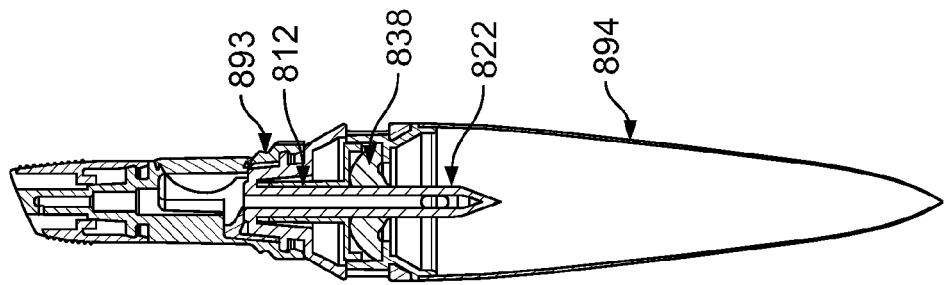
FIG. 8B
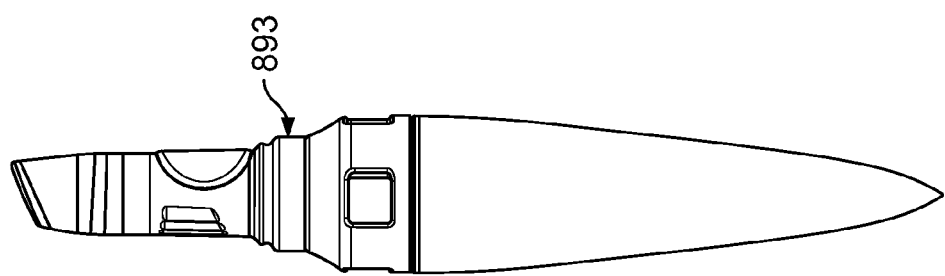
FIG. 8A
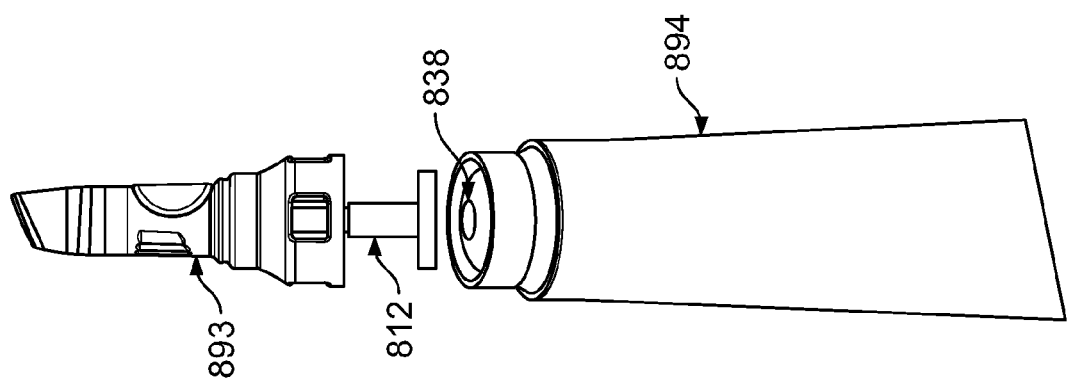

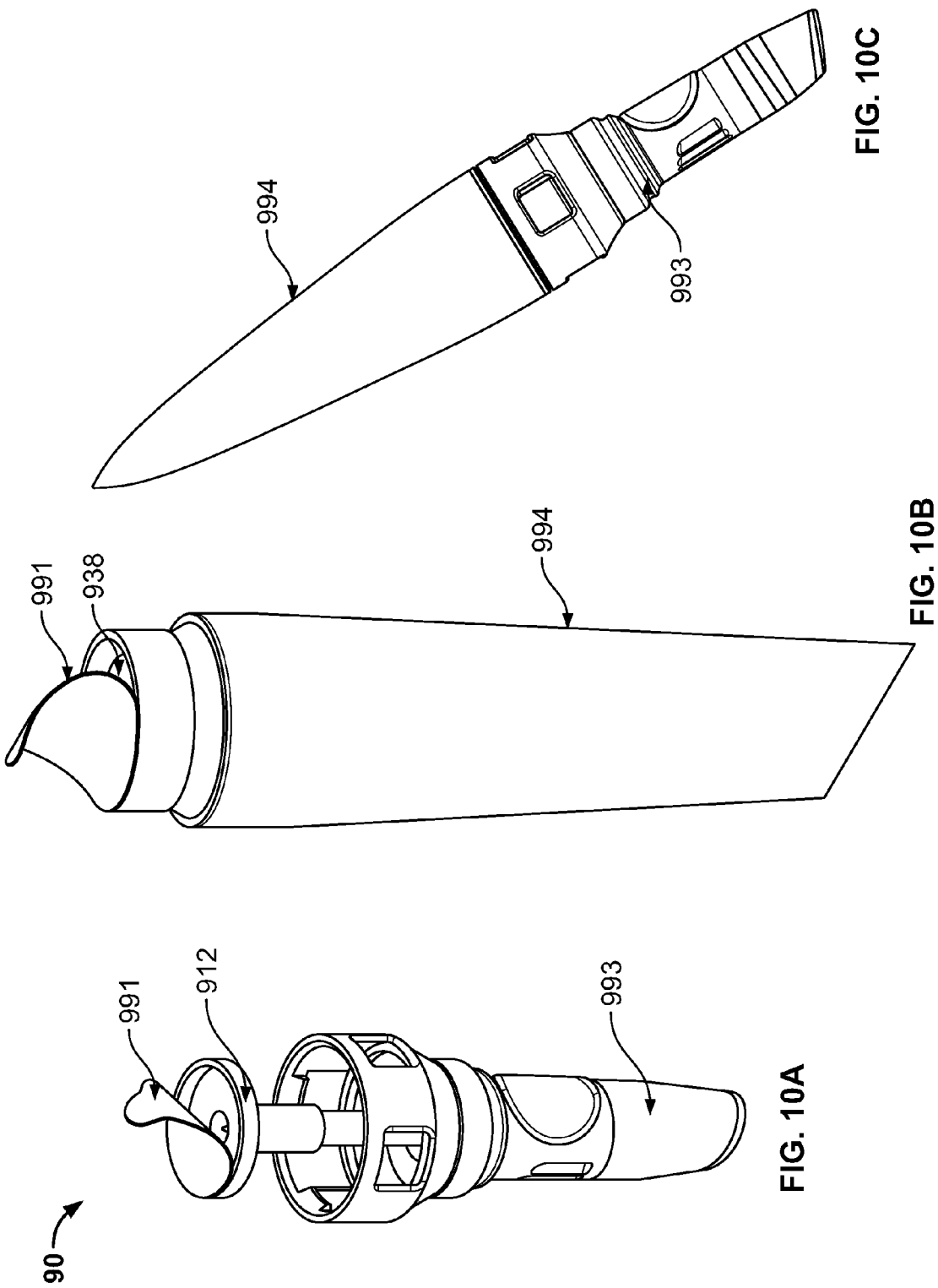

SINGLE USE CONNECTORS

CROSS-REFERENCE TO RELATED PATENT APPLICATIONS

This patent application claims benefit under 35 U.S.C. § 119 to U.S. provisional patent application Ser. No. 62/280,693, filed 19 Jan. 2016, entitled "Single Use Connectors," which is hereby incorporated by reference in its entirety as part of the present disclosure.

FIELD OF THE INVENTION

The present invention relates to a connector assembly for use in injecting or otherwise transferring a fluid or other type of substance from and/or into a container or other device (an opposing device or other device). In particular, the present invention relates to a single-use (or other) connector (or other) assembly that guards against (or otherwise reduces) contamination of the piercing member within the connector assembly and/or guards against (or otherwise reduces) re-use of the assembly and its piercing member.

BACKGROUND INFORMATION

A typical prior art connector assembly piercing member has a sharp tip in order to transfer a substance from or into an opposing device. One of the drawbacks of prior art piercing members is that users may accidentally prick themselves with an exposed piercing member present in the connector assembly. One level of concern relates to the pain and potential physical injury associated with an accidental piercing member prick.

A second and much more dangerous situation arises if the piercing member of the connector assembly has been previously used. For example, if a connector assembly has already been used and been contaminated by germs or contaminants, the germs or contaminants may thereafter be transmitted into the next opposing device pricked with the same piercing member present in the connector assembly. Often times it is very difficult to determine with certainty whether a prior art connector assembly is used or unused once out of its original packaging.

It is an object of at least some embodiments of the present invention to overcome one or more of the above-described drawbacks and/or disadvantages of the prior art.

SUMMARY OF THE INVENTION

In accordance with a first aspect, the present invention is directed to a connector comprising: a first piece; a piercing member attached to the first piece; and a second piece, the piercing member being slidingly receivable within the second piece; wherein the piercing member and the second pierce are movable relative to each other between a first position where the second pieces closes the flow port and a second position where the flow port is open; the first piece further including a locking mechanism adapted to lockingly connect the first piece to a device when engaged therewith, thereby preventing subsequent disconnection of first piece and the device.

In some embodiments, upon said engagement of the first piece and the device, the second piece is moved from the first position to the second position.

In some embodiments, the locking mechanism comprises an inward lip on the first piece.

In some embodiments, the inward lip is adapted to engage an outward lip on the device after the outward lip slides past the inward lip.

In some embodiments, the first piece comprises an inner surface and the second piece comprises a stop surface that makes contact with the inner surface to stop the piercing member from further axial movement relative to the device once the inward lip engages the outward lip.

In some embodiments, the connector is partially enclosed within a dispensing head.

In some embodiments, the dispensing head includes a one-way valve and a manually-engageable actuator.

In some embodiments, the dispensing head is attachable to a squeeze tube.

In some embodiments, the connector further comprises a removable seal on the second piece.

In some embodiments, the locking mechanism cannot be unlocked.

In accordance with another aspect, the present invention is directed to a connector assembly comprising: a first piece; a piercing member attached to the first piece and having a flow port; and a second piece; wherein the piercing member is slidingly receivable within the second piece, wherein the piercing member and the second pierce are movable relative to each other between a first position where the second pieces closes the flow port and a second position where the flow port is open; the first piece including a locking mechanism that lockingly engages with a device when connected thereto, preventing subsequent disconnection of first piece and the device.

In some embodiments, upon initial connection of the first piece to the device, the second piece is moved from the first position to the second position.

In some embodiments, the locking mechanism comprises an inward lip on the first piece.

In some embodiments, the inward lip is adapted to engage an outward lip on the device after the outward lip slides past the inward lip.

In some embodiments, the first piece comprises an inner surface and the second piece comprises a stop surface that makes contact with the inner surface to stop the piercing member from further axial movement relative to the device once the inward lip engages the outward lip.

In some embodiments, the connector assembly is partially enclosed within a dispensing head.

In some embodiments, the dispensing head includes a one-way valve and a manually-engageable actuator.

In some embodiments, the dispensing head is attachable to a squeeze tube.

In some embodiments, the connector assembly further comprises a removable seal on the second piece.

In some embodiments, the locking mechanism cannot be unlocked.

In accordance with another aspect, the present invention is directed to a device including a penetrable septum moveable between (i) a first position, wherein the penetrable septum is uncompressed, and (ii) a second position, wherein the penetrable septum is compressed; and a single use connector assembly including a piercing member attached to a first piece, with the piercing member slidingly receivable within a second piece, wherein at least one of the piercing member and the penetrable septum is axially moveable with respect to the other of the piercing member and the penetrable septum in an unlocked position prior to and during usage of the connector, and the at least one of the piercing member and the penetrable septum is no longer axially moveable with respect to the other of the piercing member and the penetrable septum in a locked position.

In some embodiments, upon said engagement of the first piece and the device, the second piece is moved from the first position to the second position.

In some embodiments, the connector assembly is partially enclosed within a dispensing head.

In some embodiments, the dispensing head includes a one-way valve and a manually-engageable actuator.

In some embodiments, the dispensing head is attachable to a squeeze tube.

In some embodiments, the connector assembly further comprises a removable seal on the second piece.

In accordance with another aspect, the present invention is directed to a method comprising: inserting a piercing member of a connector assembly into a penetrable septum, the connector assembly further including a first piece attached to the piercing member, and a second piece, wherein the piercing member is slidingly received within the second piece; and locking the piercing member of the connector in the penetrable septum.

In some embodiments, the locking comprises fixing relative positioning of the piercing member and the penetrable septum such that neither is axially moveable with respect to the other.

In some embodiments, the locking is permanent.

Other objects, features and/or advantages will become apparent in view of the following detailed description of the embodiments and the accompanying drawings.

However, while various objects, features and/or advantages have been described in this Summary and/or will become more readily apparent in view of the following detailed description and accompanying drawings, it should be understood that such objects, features and/or advantages are not required in all aspects and embodiments.

This Summary is not exhaustive of the scope of the present aspects and embodiments. Thus, while certain aspects and embodiments have been presented and/or outlined in this Summary, it should be understood that the present aspects and embodiments are not limited to the aspects and embodiments in this Summary. Indeed, other aspects and embodiments, which may be similar to and/or different from, the aspects and embodiments presented in this Summary, will be apparent from the description, illustrations and/or claims, which follow.

It should also be understood that any aspects and embodiments that are described in this Summary and do not appear in the claims that follow are preserved for later presentation in this application or in one or more continuation patent applications.

It should also be understood that any aspects and embodiments that are not described in this Summary and do not appear in the claims that follow are also preserved for later presentation or in one or more continuation patent applications.

BRIEF DESCRIPTION OF THE DRAWINGS

FIGS. 4A, 4B show perspective cross-sectional views of the connector assembly attached to both ends of a conduit;

FIGS. 5A, 5C are perspective views, and FIGS. 5B, 5D are corresponding perspective cross-sectional views of the connector assembly attached to one end of a conduit;

FIG. 6A is a perspective view and FIG. 6B is a corresponding perspective cross-sectional view of the connector assembly attached to one end of a conduit, while FIGS. 6C, 6D are perspective partial cross-sectional views of the connector assembly attached to one end of the conduit;

FIG. 7A is a perspective view of the connector assembly attached to a conduit and a pouch that the conduit attaches to, while

FIG. 8A is a perspective view of the connector assembly that forms part of a dispensing head that attaches to a tube, while FIG. 8B is a perspective cross-sectional view of the embodiment of FIG. 8A;

FIG. 10A is a perspective view of the embodiment of the dispensing head of FIG. 9A with the seal being peeled off; FIG. 10B is a perspective view of the tube of FIG. 9B with the seal being peeled off; and FIG. 10C is a perspective view showing the dispensing head of FIG. 10A attached to the tube of FIG. 10B;

DETAILED DESCRIPTION OF EMBODIMENTS OF THE INVENTION

Figure 1C:
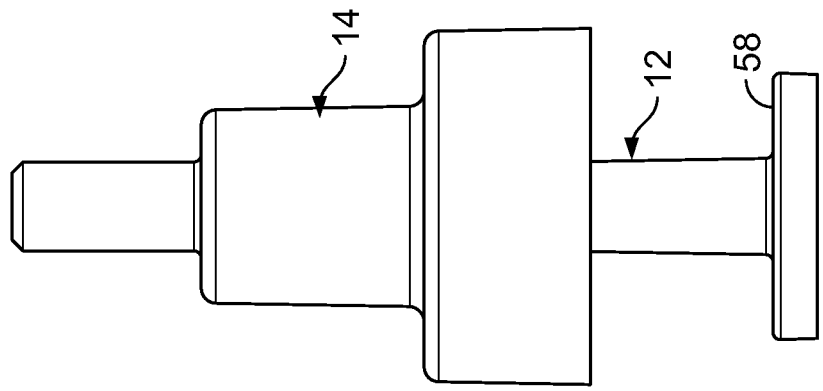
FIG. 1C is a perspective view of the connector assembly of FIG. 1A with the piercing member of the first piece inserted into a friction fit sleeve of the second piece.
Figure 1B:
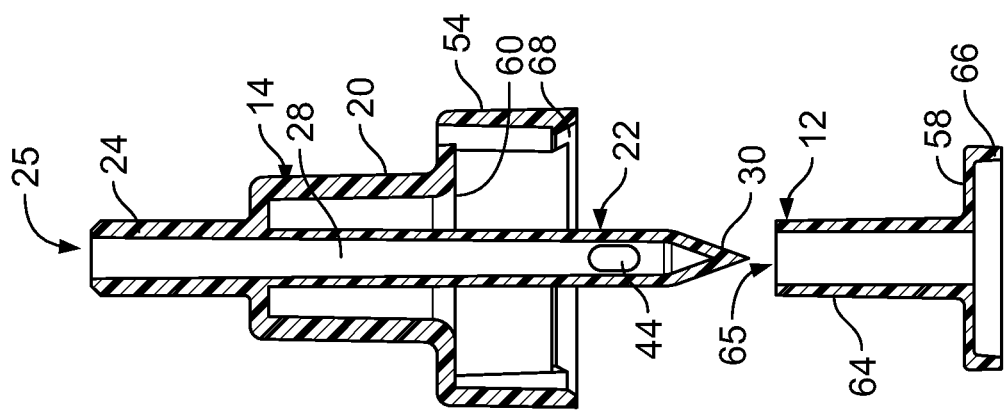
FIG. 1B is a perspective cross-sectional view of the connector assembly of FIG. 1A.
Figure 1A:
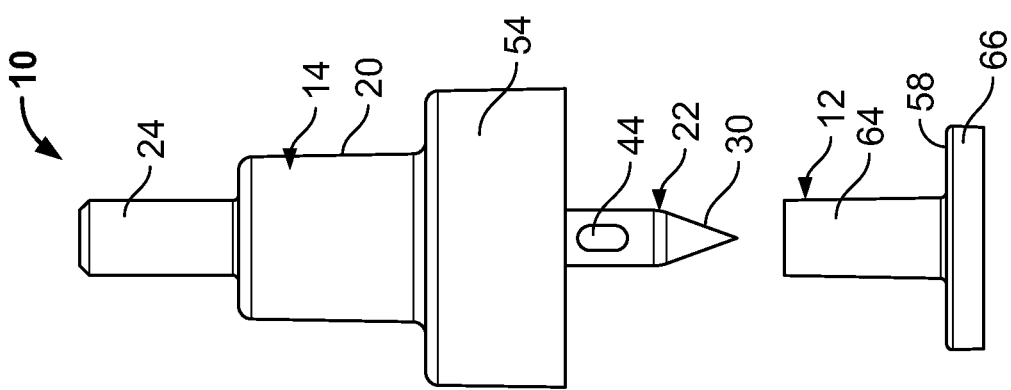
FIG. 1A is a perspective view of a single use connector assembly embodying the present invention including a piercing member attached to a first piece and a second piece.

In FIG. 1A, a device is indicated generally by the reference numeral 10. In the illustrated embodiment, the device 10 is a single use connector assembly. However, as may be recognized by those skilled in the pertinent art based on the teachings herein, the invention may be embodied in and otherwise may be applicable to devices other than connector assemblies, such as, for example, cannula and probe assemblies.

As shown in FIGS. 1A-1C, the connector assembly 10 comprises a first piece 14, a second piece 12, a piercing member 22 centered and enclosed within the first piece 14. In the illustrated embodiment, the connector assembly 10 is used for administering a substance from or into a chamber of a container. However, as may be recognized by those of ordinary skill in the pertinent art based on the teachings herein, the connector assembly may be used for any of numerous applications currently known, or that later becomes known, such as, for example, filling a container with a substance, dispensing a substance from or into an opposing device, and any form of fluid transfer. As also may be recognized by those of ordinary skill in the pertinent art based on the teachings herein, the connector assembly is attachable to any of numerous devices, currently known or that later become known, capable of performing the function of a container as described herein.

The first piece 14 includes a tubular end 24 with a centered (or otherwise) opening 25 therein, a shell 20, and a wide (or otherwise) opening 54 at the end opposite to the tubular end 24. The tubular end 24 may be in fluid communication with a conduit or a chamber (not shown) attached thereto. As better shown in FIG. 1B, the first piece 14 further includes a piercing member 22. The piercing member 22 includes a hollow shaft 28 with a tip 30 formed at a dispensing end of the shaft, two or more ports 44 displaced from the tip 30 of the shaft, the ports being in fluid communication with an interior of the hollow shaft 28. In the illustrated embodiment, the piercing member tip 30 is defined by a non-coring, conically-pointed tip; however, as may be recognized by those of ordinary skill in the pertinent art based on the teachings herein, the tip may define any of numerous other tip configurations that are currently known, or that later become known, such as, for example, a trocar tip. Additionally, the tip may be metal or plastic, such as, for example, a tip made of Graphene or Vectra. The piercing member may be metal, plastic, such as Graphene or Vectra, or may be made of a flexible polymer, such as a biocompatible polymer. In the illustrated embodiment, the two ports 44 are diametrically opposed relative to each other; however, as may be recognized by those of ordinary skill in the pertinent art based on the teachings herein, the piercing member may define any number of ports (i.e., one or more ports) that may define any of numerous different configurations and locations. In the illustrated embodiment, the piercing member 22 is integrally molded with the first piece 14; however, as may be recognized by those of ordinary skill in the pertinent art based on the teachings herein, the piercing member may be fixedly attached to the first piece in any of numerous other configurations that currently known, or that later becomes known. Exemplary piercing members are disclosed in co-pending U.S. patent application Ser. No. 13/864,919 entitled "Self Closing Connector," claiming priority to similarly-titled U.S. Provisional Patent Application Ser. No. 61/635,258, filed Apr. 18, 2012, and similarly-titled U.S. Provisional Patent Application Ser. No. 61/625,663, filed Apr. 17, 2012, all of which are hereby expressly incorporated by reference in their entireties as part of the present disclosure.

The second piece 12 includes a friction (or otherwise) fit sleeve 64 with a centered (or otherwise) opening 65 formed therein and attached to and in fluid communication with an alignment cup 66, and a stop surface 58 configured to align with and make contact with a parallel (or otherwise) inner surface 60 within the wide opening 54 of the first piece 14. The opening formed within the friction (or otherwise) fit sleeve 64 frictionally (or otherwise) receives a distal end of the piercing member 22 to align and guide the piercing member tip 30 and/or prevent deflection thereof. The friction fit sleeve 64 further operates to protect (at least a portion of) the piercing member and to close off the ports 44 of the piercing member prior to usage of the connector assembly. In some embodiments, the friction fit sleeve 64 may be formed of a relatively flexible material. At the wide opening side of the first piece 14, the rim of the inner opening of the wide opening 54 defines an (at least partly) annular (or otherwise) snapping lip 68, further described below with respect to a container (or other device) to which the connector assembly 10 may be attached.

Figure 2A:
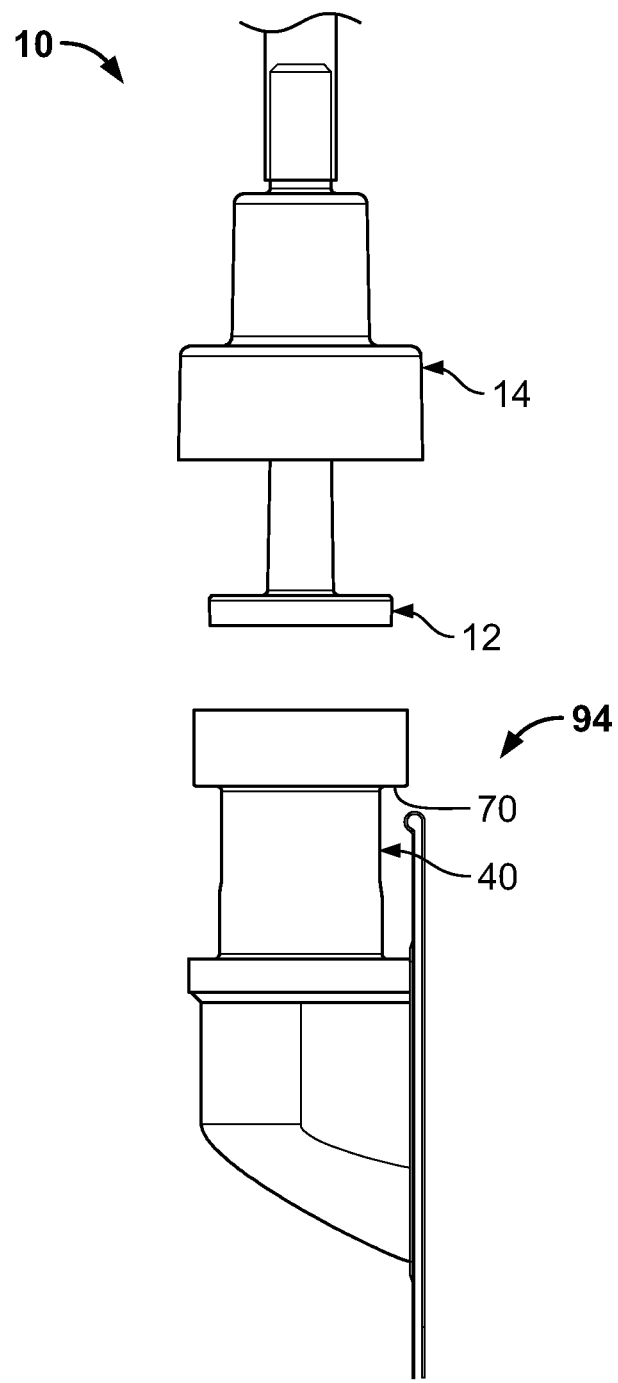
FIG. 2A is a perspective view of the connector assembly of FIG. 1 prior to attachment to an opening of a chamber of a container.
Figure 2B:
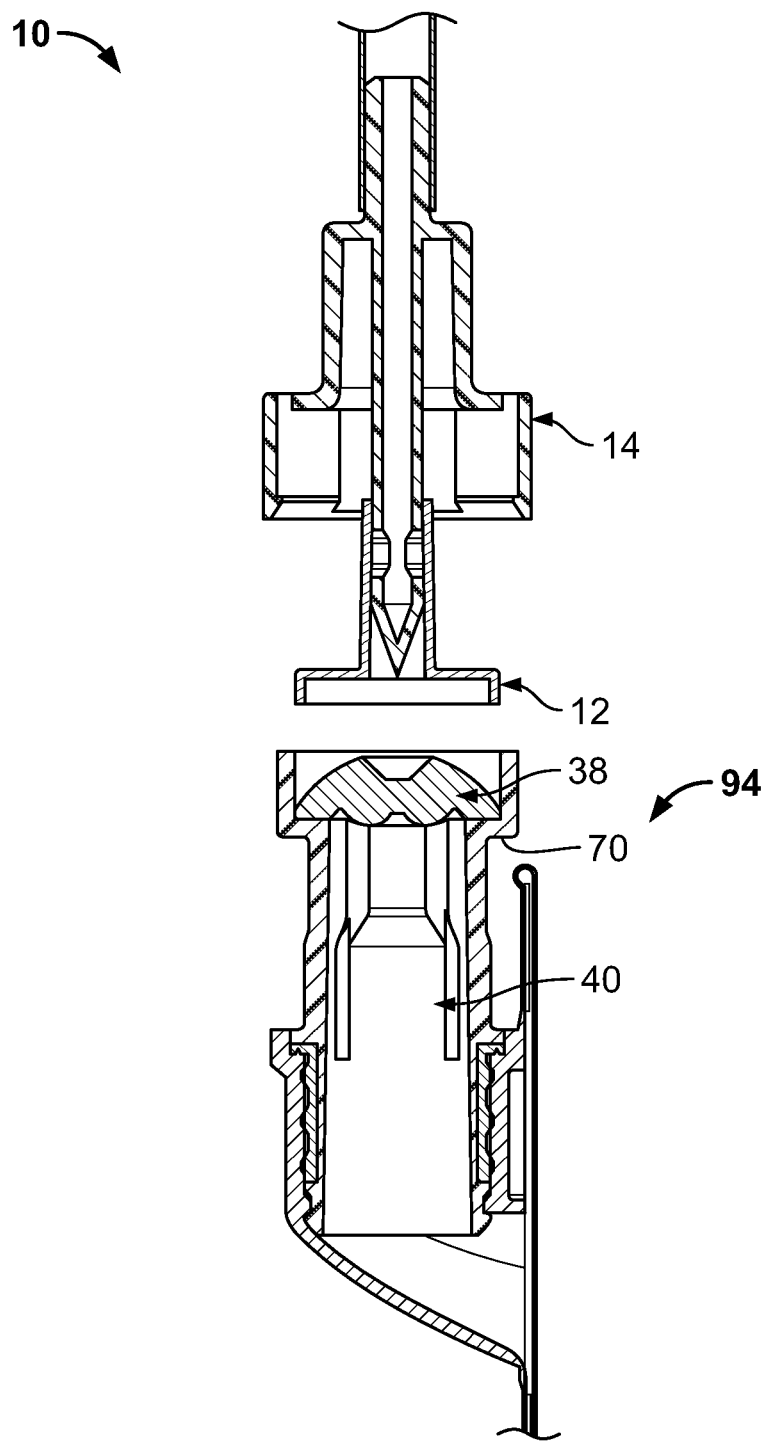
FIG. 2B is a perspective cross-sectional view of the connector assembly and the opening of the chamber of the container of FIG. 2A.
Figure 2C:
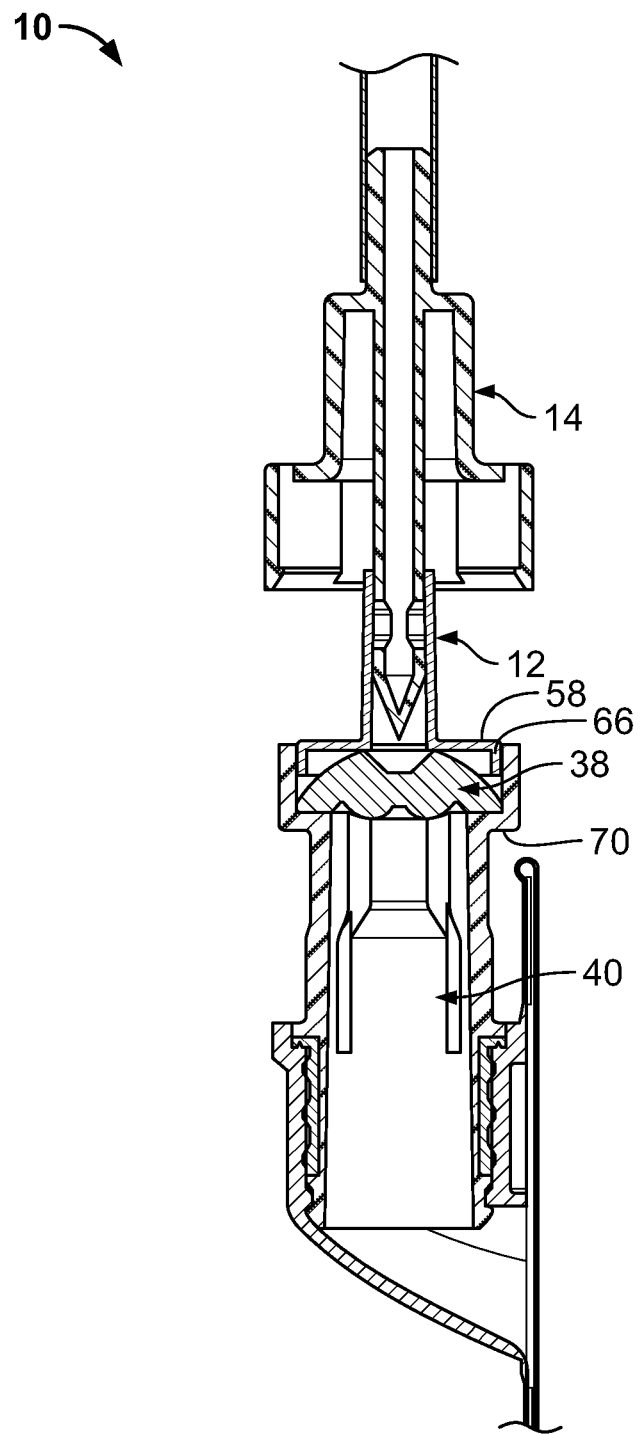
FIG. 2C is a perspective cross-sectional view of the connector assembly upon making contact with the opening of the chamber of FIG. 2A.

FIGS. 2A-2B show the connector assembly 10 and a container (or other device) 94 to which the connector assembly 10 may be attached. In the illustrated embodiment, the container 94 includes a chamber 40 having an opening. As shown in FIG. 2B, the opening of the chamber 40 of the container comprises a penetrable septum or stopper 38 in fluid communication with and sealing the chamber 40. In the illustrated embodiment, the proximal end of the penetrable septum 38 frictionally fits about the distal end of the opening of the chamber 40.

Figure 2D:
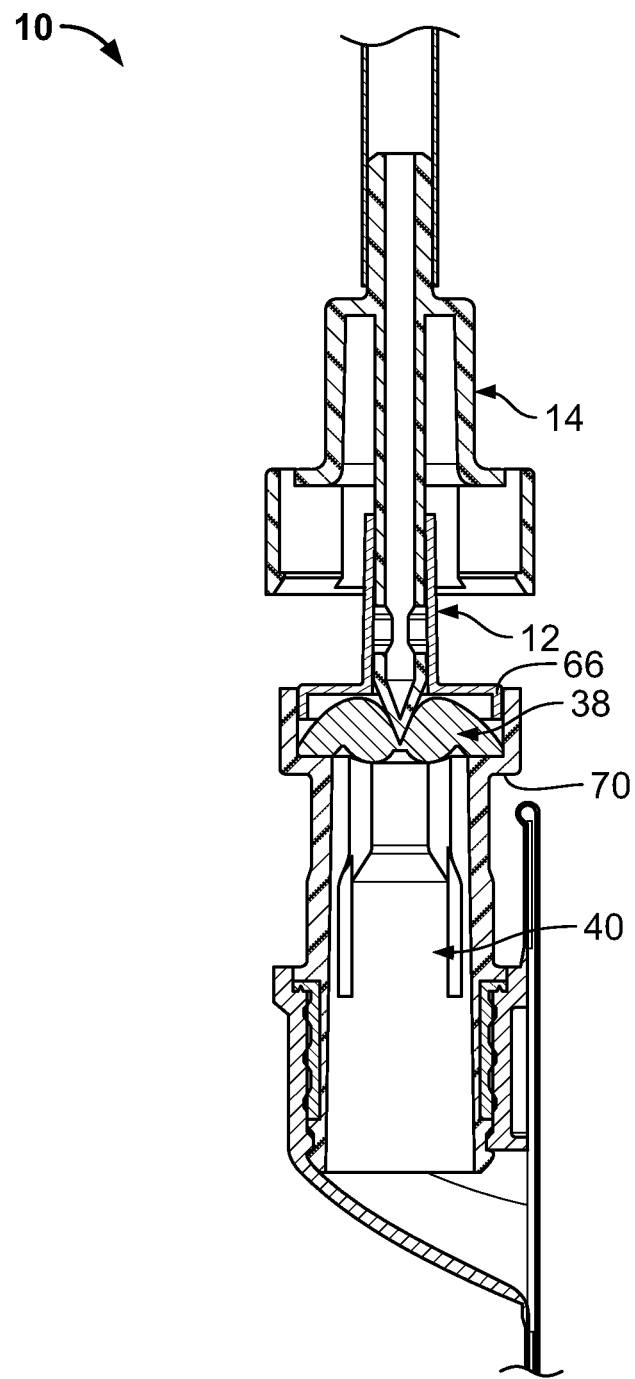
FIG. 2D is a perspective cross-sectional view of the connector assembly of FIG. 2A further depressed against the container, prior to penetration by the piercing member.
Figure 2E:
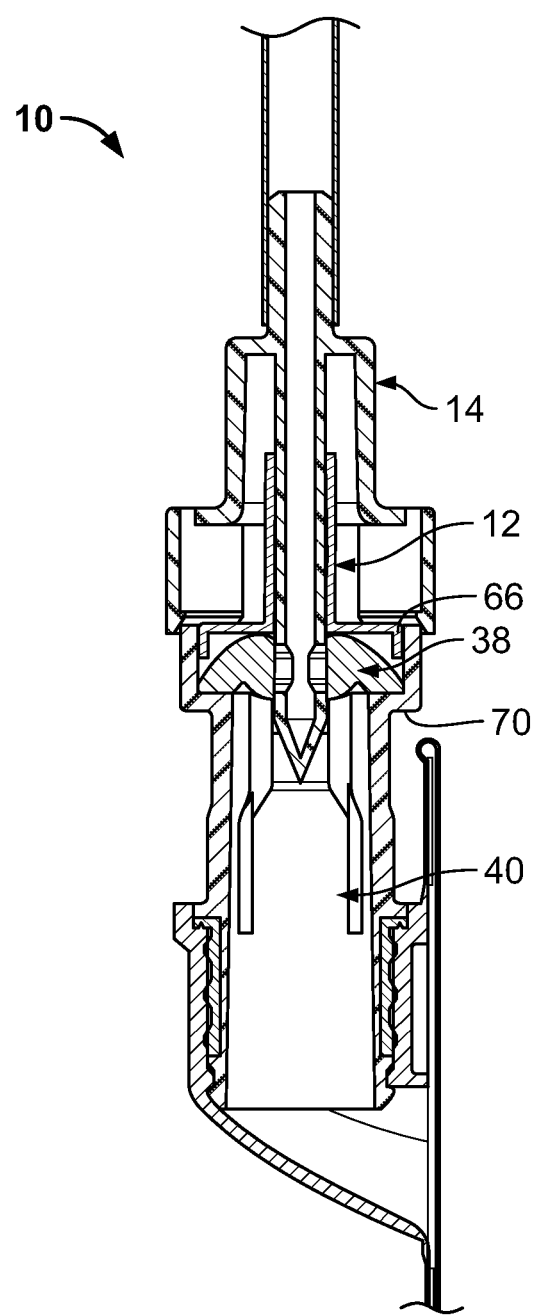
FIG. 2E is a perspective cross-sectional view of the connector assembly of FIG. 2A, wherein the piercing member has penetrated the penetrable septum located at the opening of the chamber.
Figure 2F:
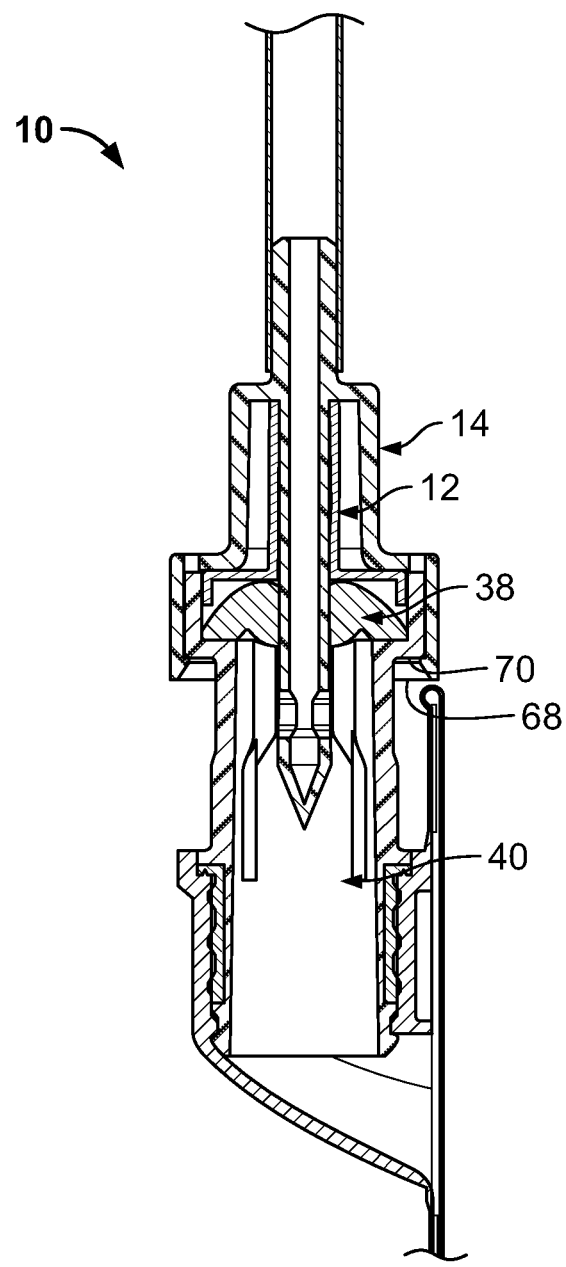
FIG. 2F is a perspective cross-sectional view of the connector assembly of FIG. 2A, when a port of the piercing member is exposed to permit substance flow from or into the chamber.

Referring again to FIGS. 1A-1C, as is shown best in FIG. 1B, the annular snapping lip 68 (which is defined by the first piece 14) defines an inward lip on the piercing member tip 30 side of the first piece 14 that allows a corresponding (at least partly) annular (or otherwise) locking rim 70 (FIG. 2A) located at the opening of the chamber 40 of the container 94, to slide therein or otherwise into the first piece 14 with the annular snapping lip 68 snapping over the annular locking rim 70 (as shown in FIG. 2F) when the piercing member 22 slides in a direction from a distal end of a penetrable septum 38 toward a proximal end thereof, and thereafter preventing the piercing member 22 from sliding back in the opposite direction. In at least some embodiments, the (at least partly) annular (or otherwise) locking rim 70 defines an outward lip that engages the inward lip after the outward lip slides past the inward lip.) Further, the stop surface 58 of the second piece 12 makes contact with the parallel inner surface 60 within the wide opening 54 of the first piece 14 to stop the piercing member 22 from further axial movement in the direction from the distal end of the septum 38 toward the proximal end thereof once the annular snapping lip 68 snaps over the annular locking rim 70 (as shown in FIG. 2F). Consequently, once the annular snapping lip 68 snaps over the annular locking rim 70, the piercing member is locked within the septum 38.

In the illustrated embodiment, the septum 38 comprises a substantially dome-shaped portion over a cylindrical portion and is formed of a resilient and/or elastomeric material. The approximately dome-shaped portion and/or the material (resilient and/or elastomeric) allow the septum 38 to move between a first position, as shown in FIG. 2D, where the dome-shaped portion is uncompressed (before the second portion 12 makes contact with the septum 38), and a second position, as shown in FIG. 2E, where the dome-shaped portion is compressed (after the second portion 12 makes contact with the septum 38), and later pierced by the piercing member. As may be recognized by those of ordinary skill in the pertinent art based on the teachings herein, the penetrable septum may be configured in any of numerous configurations currently known, or that later become known, capable of performing the function of the penetrable septum as described herein, such as, for example, a bellows configuration. Exemplary penetrable septa are disclosed in the following patents and patent applications which are hereby expressly incorporated by reference as part of the present disclosure: U.S. patent application Ser. No. 08/424,932, filed Apr. 19, 1995, entitled "Process for Filling a Sealed Receptacle under Aseptic Conditions," issued as U.S. Pat. No. 5,641,004; U.S. patent application Ser. No. 09/781,846, filed Feb. 12, 2001, entitled "Medicament Vial Having a Heat-Sealable Cap, and Apparatus and Method for Filling Vial," issued as U.S. Pat. No. 6,604,561, which, in turn, claims priority from U.S. Provisional Patent Application Ser. No. 60/182,139, filed Feb. 11, 2000, entitled "Heat-Sealable Cap for Medicament Vial;" U.S. patent application Ser. No. 10/655,455, filed Sep. 3, 2003, entitled "Sealed Containers and Methods of Making and Filling Same," issued as U.S. Pat. No. 7,100,646, which, in turn, claims priority from similarly titled U.S. Provisional Patent Application Ser. No. 60/408,068, filed Sep. 3, 2002; and U.S. patent application Ser. No. 10/766,172, filed Jan. 28, 2004, entitled "Medicament Vial Having a Heat-Sealable Cap, and Apparatus and Method for Filling the Vial," issued as U.S. Pat. No. 7,032,631, which, in turn claims priority from similarly titled U.S. Provisional Patent Application Ser. No. 60/443, 526, filed Jan. 28, 2003 and similarly titled U.S. Provisional Patent Application Ser. No. 60/484,204, filed Jun. 30, 2003.

However, the configuration of the septum is not limited to the above. Moreover, in some embodiments, the septum may not move between a first position and a second position and may not have both uncompressed and compressed.

Figure 3B:
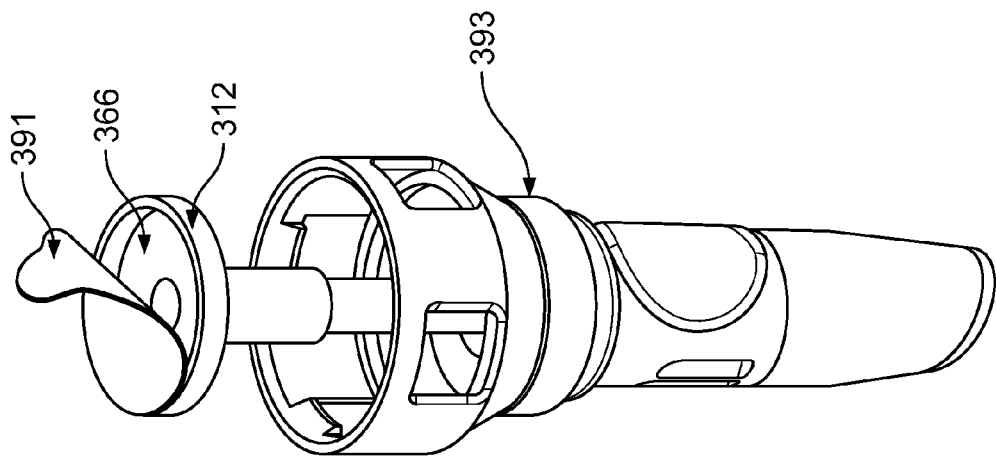
FIG. 3B is a perspective view of the connector assembly of FIG. 3A showing the removable seal being peeled away.
Figure 3A:
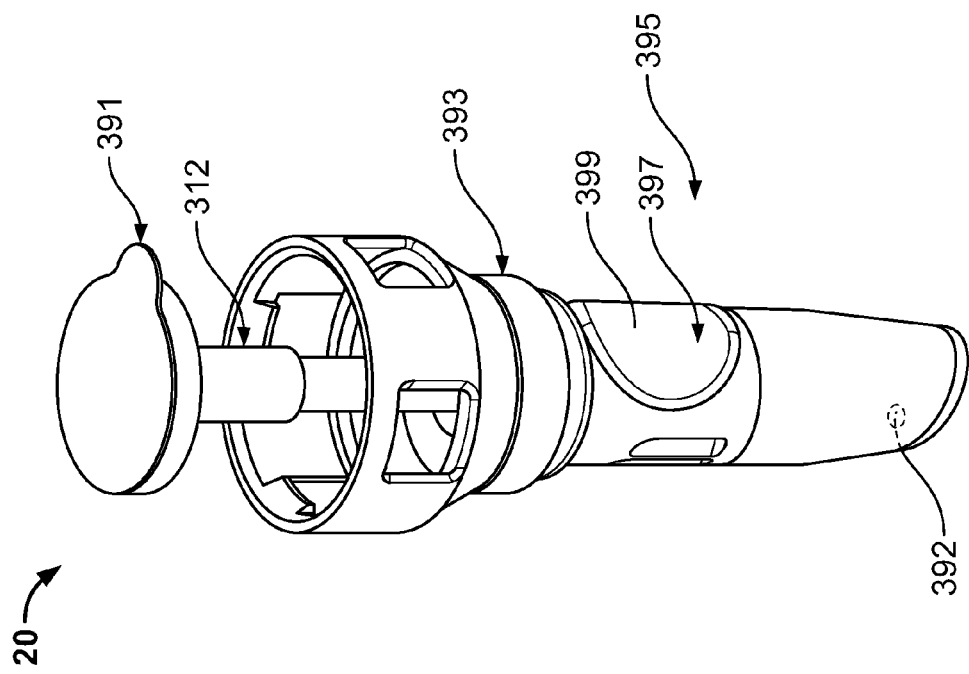
FIG. 3A is a perspective view of another embodiment of the connector assembly showing a removable seal sealing an opening of an alignment cup of the second piece of the connector assembly.

In FIGS. 3A and 3B, another connector assembly embodying the present invention is indicated generally by the reference numeral 20. The connector assembly 20 is the same as and/or substantially similar to the connector assembly 10 described above, and therefore like reference numerals are preceded by the numeral "3" to indicate like elements. The primary difference of the connector assembly 20 in comparison to the connector assembly 10 is that the connector assembly 20 is partially enclosed within a dispensing head 393 and includes a removable seal 391. The dispensing head 393 may include a valve 392 and an actuating pump 395. Exemplary such valves and actuating pumps are disclosed in the following patents and patent applications which are hereby expressly incorporated by reference as part of the present disclosure: U.S. application Ser. No. 11/237,599 filed Sep. 27, 2005, titled "Laterally-Actuated Dispenser with One-Way Valve for Storing and Dispensing Metered Amounts of Substances," now U.S. Pat. No. 7,665,923 issued Feb. 23, 2010, and claiming priority to U.S. Provisional Application No. 60/613,583, filed Sep. 27, 2004, titled "Laterally-Actuated Dispenser with One-Way Valve for Storing and Dispensing Metered Amounts of Substances" and U.S. Provisional Application No. 60/699, 607 filed Jul. 15, 2005 titled "Laterally-Actuated Dispenser with One-Way Valve for Storing and Dispensing Metered Amounts of Substances."

In some embodiments, the valve 392 comprises a one-way valve (which may form an external portion of the dispensing head) and including a valve seat (which may extend axially) and a valve cover (which may be flexible and/or extend axially) seated on the valve seat and defining a normally-closed, seam (which may extend axially) therebetween forming a fluid-tight seal between the valve cover and valve seat, wherein the valve cover is movable relative to the valve seat and the seam is connectable in fluid communication with an outlet aperture to allow the passage of substance through the seam and out of the dispenser.

In some embodiments, the actuating pump 395 comprises a manually-engageable actuator 397 having a manually-engageable surface 399 on an external side of the manually-engageable actuator 397 and further having an underside that defines or functions as a piston movable between first and second positions relative to a compression chamber (within the dispensing head and/or in fluid communication with the one-way valve) to pressurize substance within such compression chamber. In some embodiments, (i) during movement in the direction from the second position toward the first position, a variable-volume storage chamber is in fluid communication with the compression chamber for permitting substance to flow from the variable-volume storage chamber into the compression chamber, and (ii) during movement in the direction from the first position toward the second position (a) the compression chamber is not in fluid communication with the variable-volume storage chamber and (b) the substance within the compression chamber is pressurized above the one-way valve opening pressure and dispensed through the normally closed seam and out of the dispenser.

As shown in FIGS. 3A-3B with regard to an embodiment of the connector assembly 20, prior to usage, a removable seal 391 covers and seals an open end of the alignment cup 366 of the second piece 312 of the connector assembly, sealing the opening of the second piece and the piercing member (not shown) therein. In this embodiment, the first piece is partially enclosed within and forms part of a dispensing head 393. The piercing member within the second piece 312 is thereby maintained in a sterile state prior to use. Prior to attaching the connector assembly to the opening of a chamber of a container, the seal 391 is removed or peeled away from the proximal end of the alignment cup 366. In the illustrated embodiment, the seal is a foil seal. However, as may be recognized by those of ordinary skill in the pertinent art based on the teachings herein, the removable seal may take the form of any of numerous different sealing mechanisms that are currently known, or that later becomes known, such as, for example, a removable liner or a removable cap. In one embodiment, the seal 391 is a heat-sealed film, e.g., foil or plastic that has barrier properties, particularly for oxygen sensitive materials such as creams contained in the chamber 40 to prevent oxygen permeation into the material contained within the chamber. Even though not shown, the embodiment of connector assembly 10 shown in FIGS. 1A-1C too may include a removable seal 391 covering the wide opening of the second piece 312, sealing the opening of the alignment cup 366 and the piercing member therein. When the dispensing head is ready for use, the seal is removed from the alignment cup end of the connector assembly.

Further, as shown in FIGS. 2A-2B, prior to penetrating the septum 38, and right after the seal covering the alignment cup 66 is peeled off, the friction fit sleeve 64 of the second piece 12 still seals the ports 44 with respect to ambient atmosphere to thereby maintain the sterility of the ports and of the interior of the piercing member. Since the ports 44 are not exposed to the ambient atmosphere, the ports, interior of the piercing member, and fluid flowing therethrough, are not contaminated and/or are maintained sterile as the fluid is dispensed from or into the chamber 40. Thus, in at least some embodiments, the piercing member is never exposed before, during, and after substance transfer.

To initiate forming of a fluid-tight hermetic connection between the connector assembly 10 and an opening of the chamber 40, the opening in the alignment cup 66 of the connector assembly is first placed facing the penetrable septum 38, as shown in FIGS. 2A-2B. The alignment cup 66 aligns the piercing member 22 with the center of the penetrable septum 38 to facilitate center piercing of the septum by the piercing member. The connector assembly 10 is then depressed, as shown in FIGS. 2C-2F, progressively inducing the penetrable septum 38 from the first uncompressed position in FIG. 2D toward the compressed and pierced position in FIG. 2F. As shown in FIG. 2A through FIG. 2E, upon initial contact of the piercing member tip 30 with the surface of the penetrable septum 38, the annular snapping lip 68 of the first piece 14 is not yet snapped past the annular locking rim 70 of the container opening when connector assembly is first attached. As the connector assembly is depressed, the friction fit sleeve starts sliding up the piercing member further exposing the tip 30 to facilitate piercing of the septum, and the resistance of the surface of the septum to puncture induces the annular snapping lip 68 of the first piece 14 to fully engage the end of the annular locking rim 70 of the container, wherein the annular snapping lip 68 of the first piece 14 moves from abutting the end of the annular locking rim 70 to snapping into the flange portion of the annular locking rim 70, as shown in FIG. 2F. The piercing member tip 30 fully penetrates the septum 38 and the ports 44 start to emerge out of the friction fit sleeve 64, as shown in FIG. 2E. As the piercing member penetrates the septum, the contact (friction or otherwise) between the septum and the piercing member wipes (in effect) the piercing member to remove (or at least significantly reduce) any germs and other contaminants that may be present on the external surface of the piercing member, while the ports 44 remain unexposed until they pass through the septum. As the connector assembly is further depressed, frictional engagement between the opening of the alignment cup 66 and the septum 38, prevents further movement of the connector assembly relative to the septum. Further penetration of the piercing member 22 into the septum 38 causes the hollow shaft 28 and the tip 30 to further move relative to the alignment cup 66 against the bias of the septum 38 to, in turn, move the ports 44 to be fully opened within the chamber as shown in FIG. 2F. In this position, the piercing member 22 is in fluid communication with the chamber 40 permitting substances to flow out of or into the chamber 40 through the ports 44.

In at least some embodiments, the connector assembly cannot be reused once the annular locking rim 70 has fully snapped into position. The locking between the annular snapping lip 68 of the connector assembly and the annular locking rim 70 of the container prevents the piercing member 22 from moving back. Therefore, once the connector assembly 10 snaps into and locks into position as shown in FIG. 2F, it cannot be unlocked. In some embodiments, the connector assembly permits multiple intact transfers of substances out of a filled chamber 40 until the chamber is empty. After the chamber 40 is emptied, the container along with the connector assembly 10 is discarded. In other words, the connector assembly is configured for single use, is not re-used, and can only be disposed of along with the container to which it is attached. This prevents cross-contamination common in reusable prior art connectors.

The connector assembly may be used in various applications including cream/liquid dispensing, eyedroppers, dermatologic dispensers, and other substance transfers without the need to add preservatives therein to maintain sterility. The connector assembly may also be used to fill non-preserved liquids into intact closed containers. The connector assembly may further be used as an interface between an intact dispensing system and an intact container. In all applications, both the connector assembly and the opening of the chamber are sealed by film to protect them from contamination during shelf life. This permits the use of the above described connector assembly in harsh environments, such as hospitals and in non-sterile open environments.

FIGS. 4A-14E illustrate additional embodiments each of which includes one or more connector assembly. These connector assemblies are the same as and/or substantially similar to the connector assemblies 10 and/or 20 described above, and therefore like reference numerals preceded by the numerals "4" through "14" (i.e., irrespective of letter suffixes that may be included) are used to indicate like elements.

FIGS. 4A, 4B are perspective cross-sectional views of two fluid and/or other substance transfer systems (and/or assemblies) 400A, 400B, respectively. The two transfer systems 400A, 400B each include a conduit 496A, 496B, respectively, having two ends. Each transfer system further includes two connector assemblies. Transfer system 400A includes connector assemblies 410A, 410A, which may be, but are not required to be, identical to one another. Each of the connector assemblies 410A, 410A is attached to a respective one of the ends of conduit 496A. Similarly, transfer system 400B includes connector assemblies 410B, 410B, which may be, but are not required to be, identical to one another, and each of the connector assemblies 410B, 410B is attached to a respective one of the ends of conduit 496B. Three of the connector assemblies are shown in a similar state. One of the connector assemblies, i.e., the connector assembly shown attached to the lower end of the conduit in FIG. 4B, the piercing member 422B is enclosed within the second piece 412B. This protects the tip and ports of the piercing member from contamination. The conduit allows for fluid and/or other substance transfer between two chambers (not shown) that may be spaced apart from each other. In at least some embodiments, one or both of the chambers may be the same as and/or similar to chamber 40 and/or any other type of chamber. Each chamber may have a penetrable septum, with the piercing member of each connecting assembly piercing the septum and forming a fluid-tight hermetic seal with a respective chamber.

FIGS. 5A, 5C are perspective views of two fluid and/or other substance transfer systems (and/or assemblies), and FIGS. 5B, 5D are corresponding perspective cross-sectional views of the two transfer systems. Each transfer system includes a connector assembly attached to a conduit. In FIGS. 5A and 5B, the connector assembly 510A is attached to one end of the conduit while a self-sealing valve connector 598A is attached to its other end. Similarly, in FIGS. 5C and 5D, the connector assembly 510B is attached to one end of the conduit while a self-closing valve 598B is attached to its other end.

FIG. 6A is a perspective view of a fluid and/or other substance transfer system (and/or assembly) and FIG. 6B is a corresponding perspective cross-sectional view of the transfer system, which includes a connector assembly 610A attached to a conduit, while FIGS. 6C, 6D are perspective partial cross-sectional views of further fluid and/or other substance transfer systems (and/or assemblies), which include the connector assembly 610B attached to a conduit. In FIGS. 6A and 6B, the connector assembly 610A is attached to one end of the conduit with another type of self-sealing valve connector 698A being attached to its other end. FIG. 6C shows the connector assembly 610B attached to one end of the conduit and a male connector 698B attached to the other end of the conduit, while FIG. 6D shows the connector assembly 610B attached to one end of the conduit and a female connector 698C attached to the other end of the conduit. Exemplary such connectors are disclosed in the following co-pending patent applications, each of which is hereby expressly incorporated by reference as part of the present disclosure: U.S. patent application Ser. No. 14/536,566, filed Nov. 7, 2014, entitled "Device for Connecting or Filling and Method", which claims the benefit of similarly to similarly-titled U.S. Provisional Patent Application Nos. 61/641,248, filed May 1, 2012, and 61/794,255, filed Mar. 15, 2013.

Figure 7B:
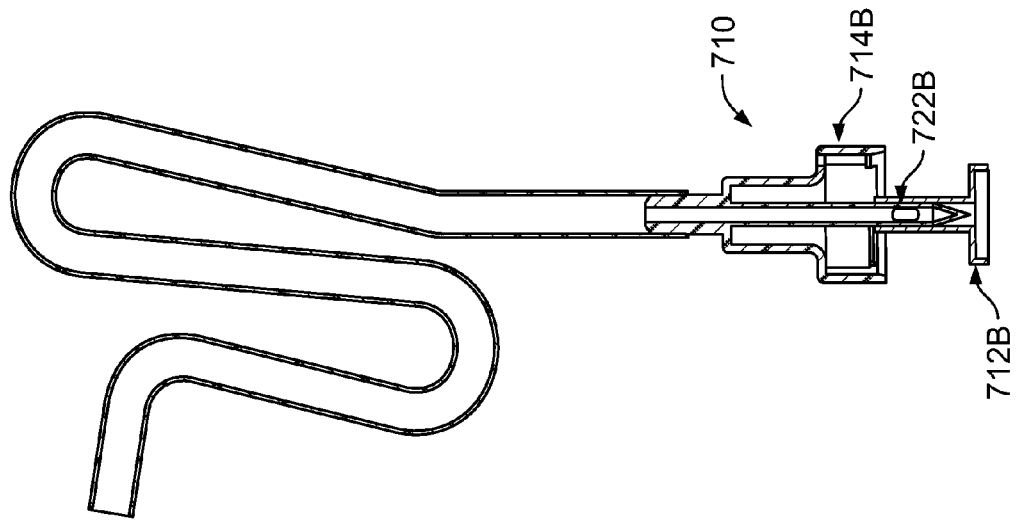
FIG. 7B is a perspective cross-sectional view of the connector assembly and the conduit shown in FIG. 7A.
Figure 7A:
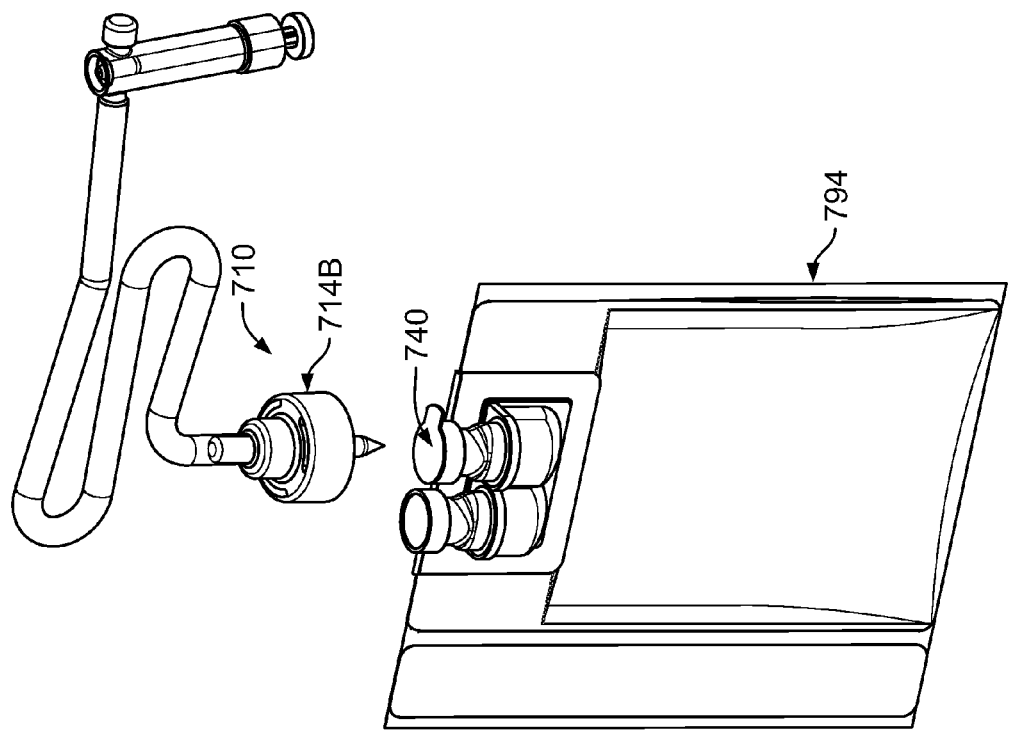

FIG. 7A is a perspective view of a fluid and/or other substance transfer system (and/or assembly), which includes a conduit, the connector assembly 710 attached to an end of the conduit and another device attached to the other end of the conduit, shown along with a pouch (or other type of container) 794 (which may include one or more chambers 740 that one or more of which) the connector assembly conduit attaches to, while FIG. 7B is a perspective cross-sectional view of the transfer system that includes the connector assembly 710 and conduit shown in FIG. 7A. Exemplary such pouches are disclosed in the following co-pending patent application, which is hereby expressly incorporated by reference as part of the present disclosure: U.S. Provisional patent application 62/280,700 entitled "Pouch with Heat-Sealed External Fitment," filed on even date herewith. The connector assembly forms a fluid-tight hermetic seal with a port 740 of the pouch to permit fluid flow therethrough.

FIG. 8A shows perspective views of an assembly, in assembled and partly disassembled states, that includes the connector assembly 20 (FIGS. 3A-3B) partially enclosed within a dispensing head 893 that attaches to a squeezable tube (or other type of container) 894 (which may include fluid and/or other substance(s) to be dispensed) to form a fluid-tight hermetic seal, while FIG. 8B is a perspective cross-sectional view of the embodiment of FIG. 8A. The dispensing head 893 is substantially similar to the dispensing head 393 explained above with respect to FIGS. 3A and 3B. The easy attachment of the dispensing head 893 to the tube 894 without exposing the piercing member to the outside allows for safe assembly by patients in hospitals and/or other harsh (or potentially harsh) environments.

Figure 9C:
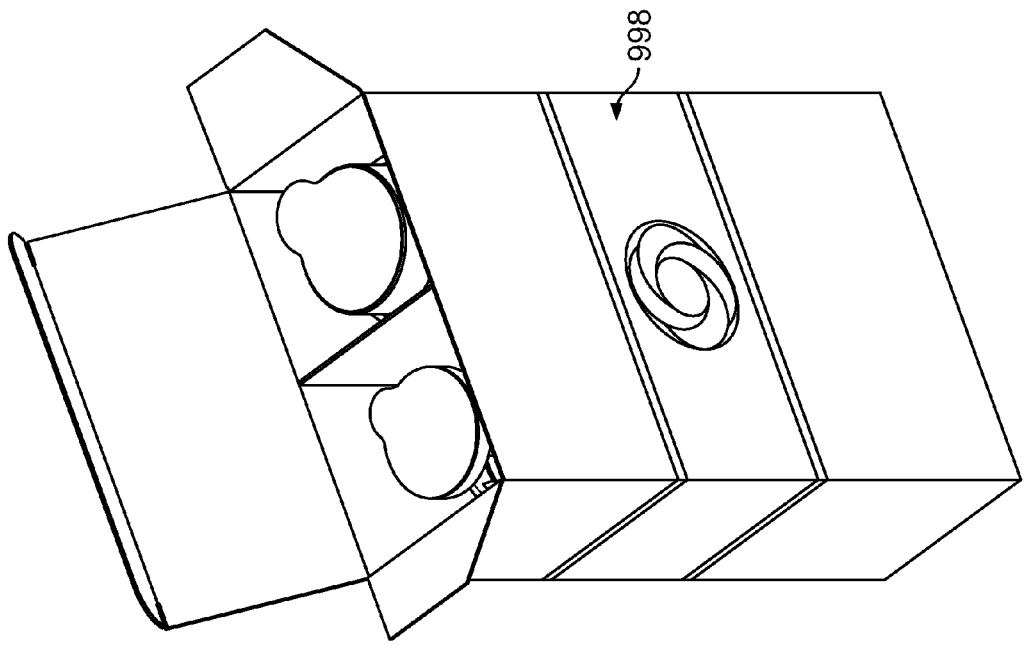
FIG. 9C is a perspective view showing a shipping kit containing the sealed connector assembly and the sealed tube.
Figure 9B:
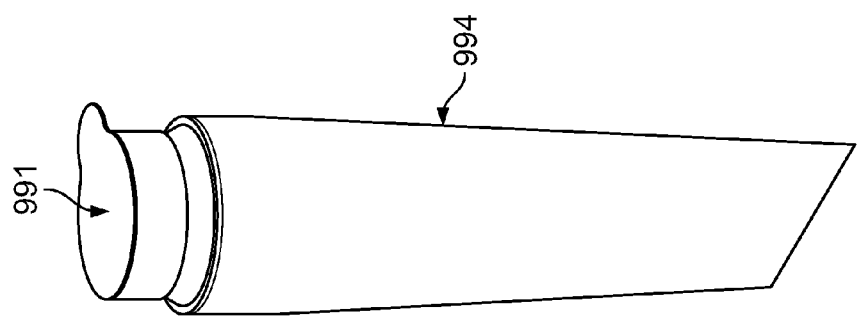
FIG. 9B is a perspective view of a sealed tube.
Figure 9A:
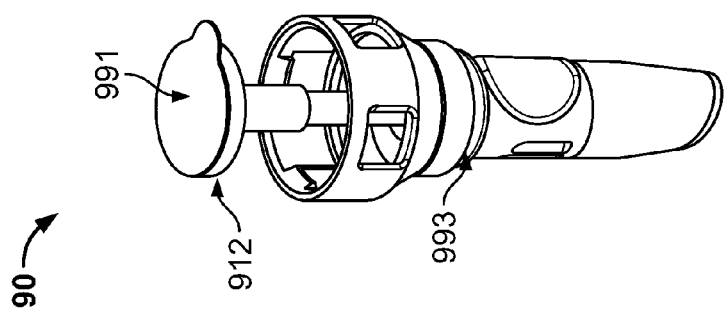
FIG. 9A is a perspective view of an embodiment of a dispensing head that attaches to a tube.

FIG. 9A is a perspective view of an embodiment of a connector assembly 90 having a sealed dispensing head 993 that attaches to a squeezable tube 994 (which may include fluid and/or other substance(s) to be dispensed), while FIG. 9B is a perspective view of a sealed tube 994, and FIG. 9C is a perspective view showing a shipping kit 998 containing the sealed dispensing head 993 and the sealed tube 994. The dispensing head 993 is substantially similar to the dispensing head 393 shown in FIG. 3A. In this embodiment, the tube 994 too is shown sealed by a removable seal 991, the removable seal being substantially similar to the removable seal 391 described above with respect to FIG. 3A. Both the sealed dispenser head and the sealed tube may be packed together in a kit as shown in FIG. 9C to facilitate easy shipment. The removable seal may act as a complete barrier preventing contact with contaminants and the ambient atmosphere thereby improving shelf life.

FIG. 10A is a perspective view of connector assembly 90 with the dispensing head 993 shown in FIG. 9A with its seal 991 in the process of being peeled off, while FIG. 10B is a perspective view of the tube 994 of FIG. 9B with its seal 991 being peeled off, and FIG. 10C is a perspective view showing the dispensing head 993 of FIG. 10A attached to the tube 994 of FIG. 10B. After a user opens the kit 998 shown in FIG. 9C, the user may peel of the removable seal 991 on the dispensing head and on the squeezable tube and connect the dispensing head to the tube to from a fluid-tight hermetic connection between the dispensing head and an opening of the tube by following the steps similar to those explained with regard to FIGS. 2A-2F.

Figure 11:
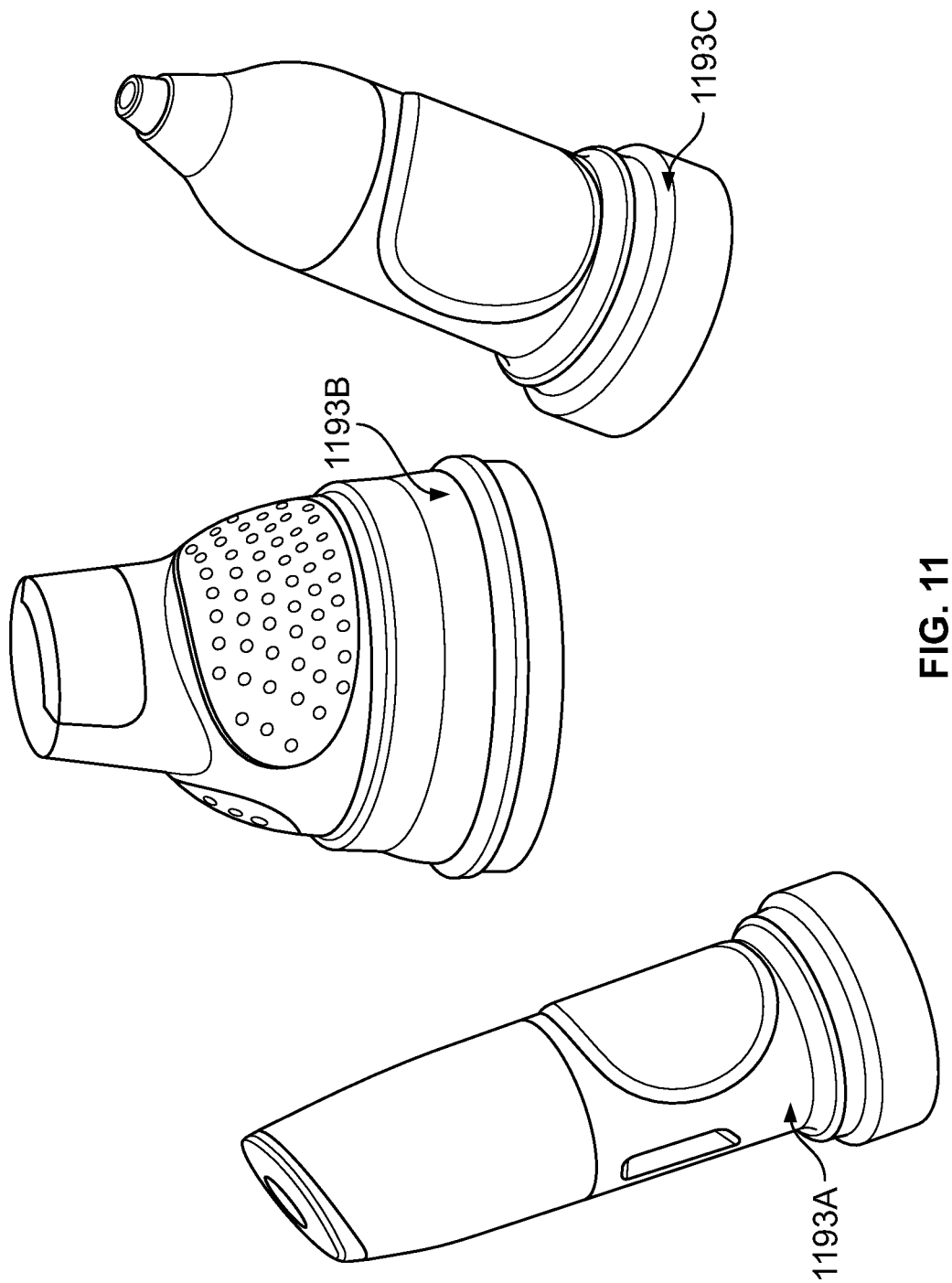
FIG. 11 shows perspective views of three alternate embodiments of dispensing heads that attach to a tube.
Figure 12C:
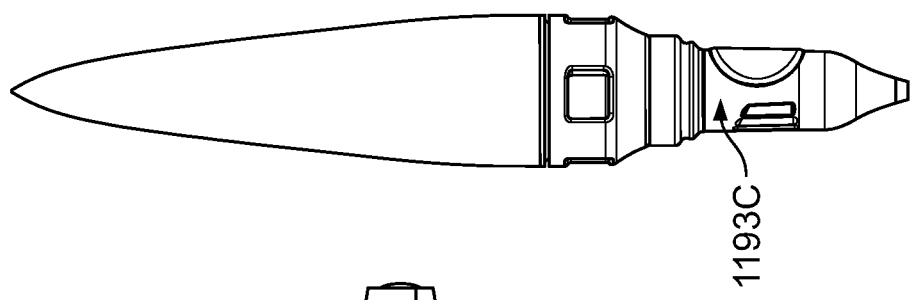
FIGS. 12A-12C are perspective views of embodiments of the dispensing heads of FIG. 11 attached to tubes.
Figure 12B:
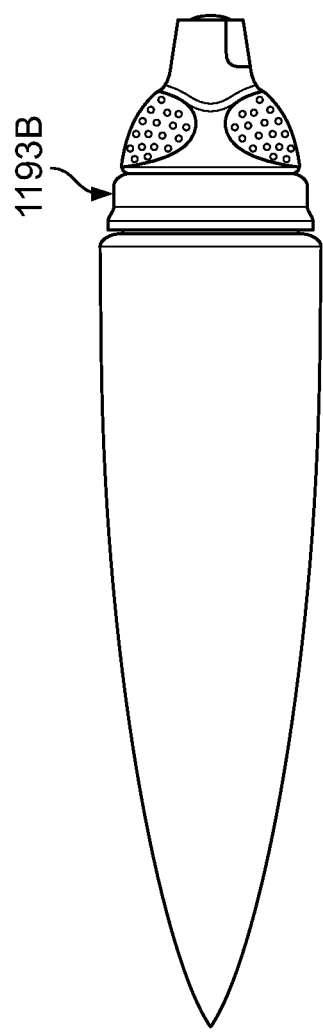
Figure 12A:
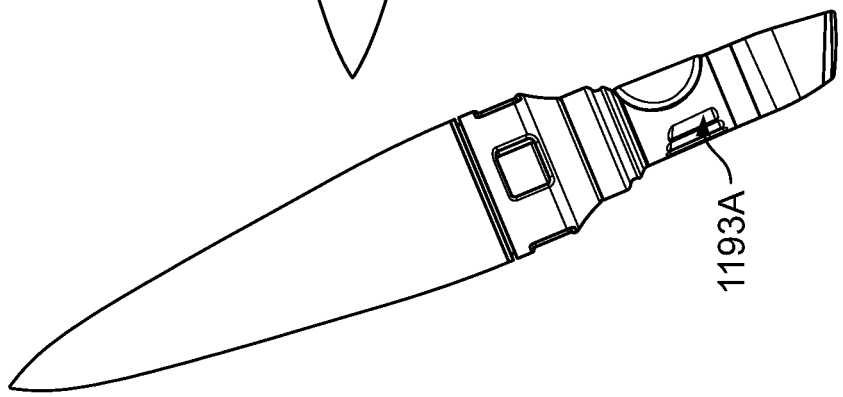

FIG. 11 shows perspective views of other embodiments of dispensing heads that may be attached to a squeezable tube and/or other type(s) of container(s) (or other type(s) of device(s)). In some embodiments, the dispensing head 1193A is configured as a surface applicator and may connect to the tube shown in FIG. 12A; the dispensing head 1193B is configured for a larger application tube and may connect to the tube shown in FIG. 12B; and, the dispensing head 1193D is configured for spot treatment and may connect to the tube shown in FIG. 12C.

Figure 13:
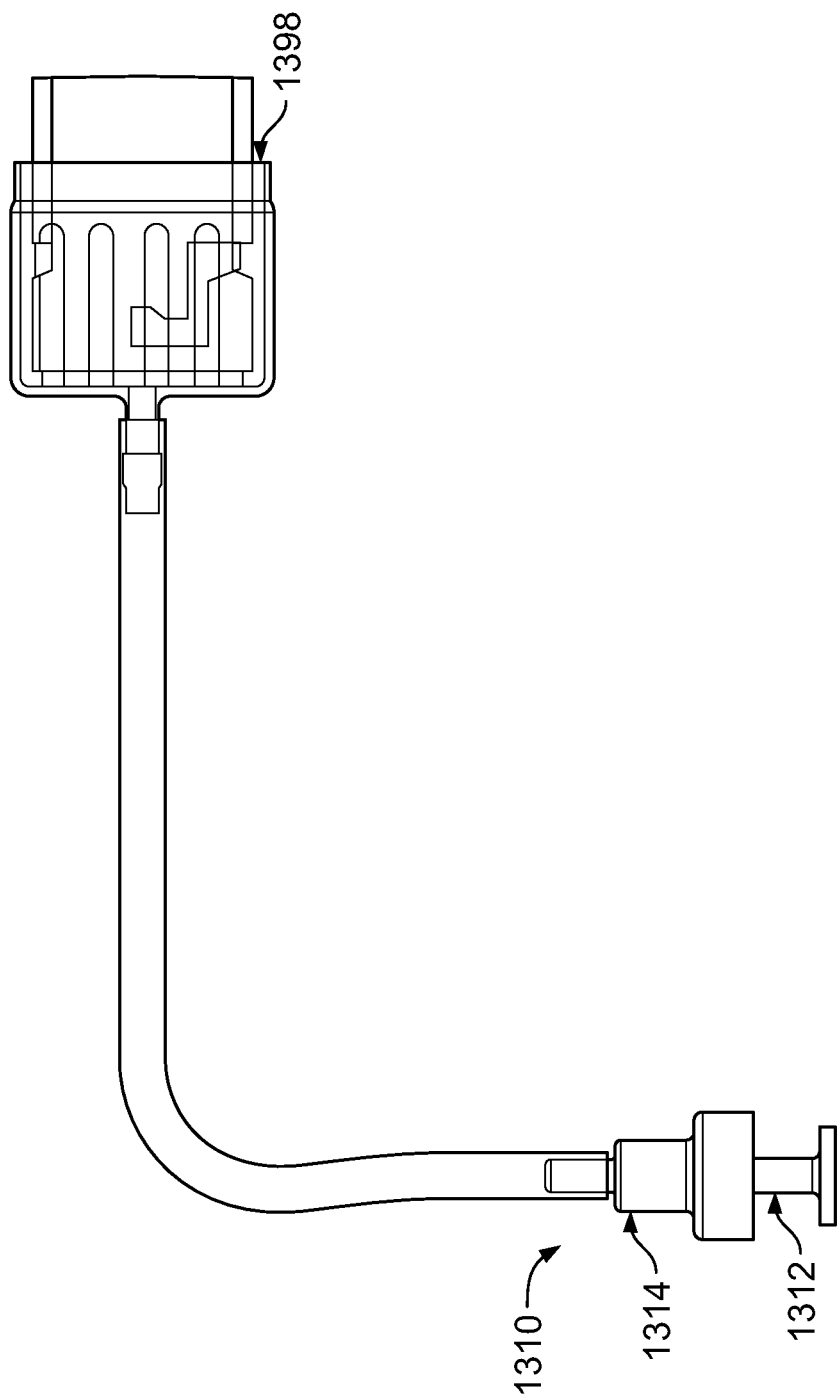
FIG. 13 is a perspective view of the connector assembly attached to one end of a conduit with an alternate connector attached to the other end of the conduit.

FIG. 13 is a perspective view of a fluid and/or other substance transfer system (and/or assembly), which includes a conduit, the connector assembly 1310 attached to one end of the conduit with an alternate connector 1398 attached to the other end of the conduit. Exemplary such alternate connectors are disclosed in the following co-pending patent applications, each of which is hereby expressly incorporated by reference as part of the present disclosure: U.S. patent application Ser. No. 13/874,839, filed May 1, 2013, entitled "Device for Connecting or Filling and Method", which claims the benefit of similarly titled U.S. Provisional Patent Application No. 61/641,248, filed May 1, 2012, and similarly titled U.S. Provisional Patent Application No. 61/794, 255, filed Mar. 15, 2013; and U.S. patent application Ser. No. 14/536,566, filed Nov. 7, 2014, entitled "Device for Connecting or Filling and Method", which claims the benefit of similarly to similarly-titled U.S. Provisional Patent Application Nos. 61/641,248, filed May 1, 2012, and 61/794,255, filed Mar. 15, 2013.

Figure 14E:
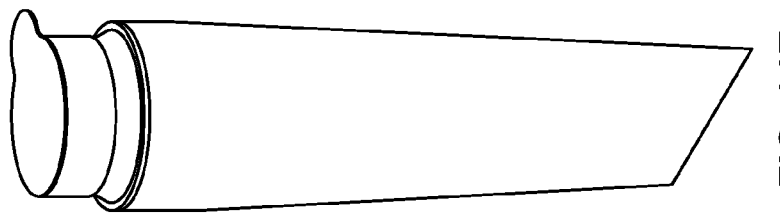
FIGS. 14A, 14C, 14D and 14E show additional perspective views of the connector assembly and of the tube that it connects to, and FIG. 14B is a perspective cross-section view of the tube shown to be empty.
Figure 14D:
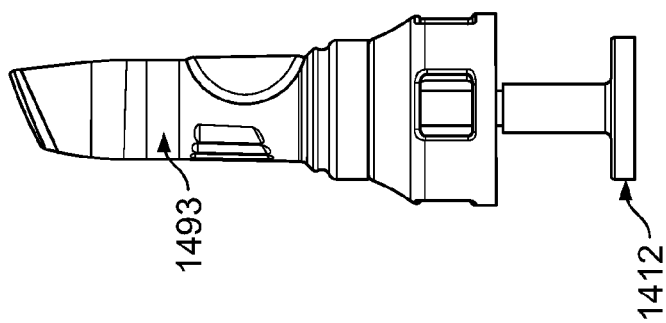
Figure 14C:
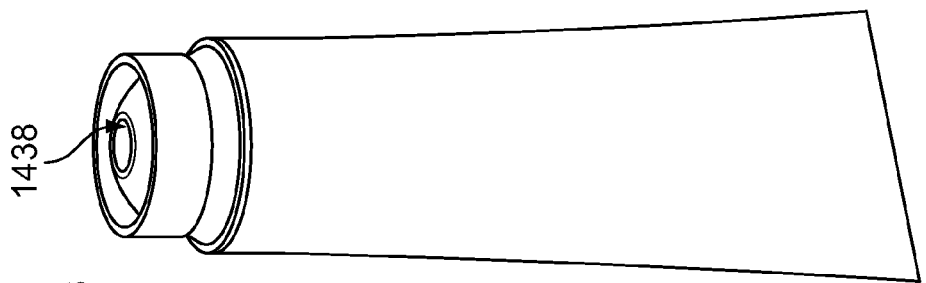
Figure 14B:
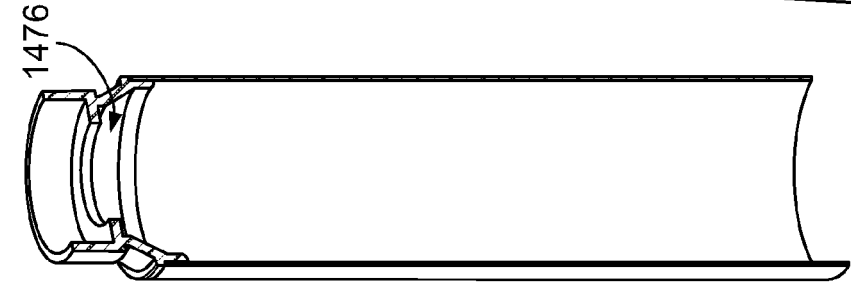
Figure 14A:
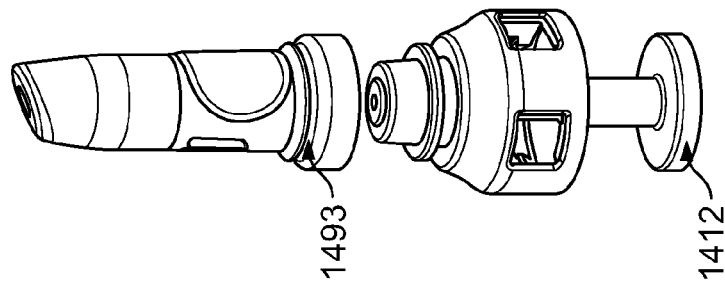

FIGS. 14A, 14C, 14D and 14E show additional perspective views of an embodiment of the dispensing head 1493 and an embodiment of the squeezable tube that it may be used to connect to, while 14B is a perspective cross-section view of one embodiment of the squeezable tube. FIG. 14B shows a groove 1496 wherein the septum 1438 is received in at least some embodiments.

In at least some embodiments, one or more portions of one or more embodiments disclosed herein may be embodied in a method, an apparatus, a connector, a coupler, a conduit, a transport, device, a dispenser, an assembly, a kit, a system and/or any combination thereof.

It should be understood that the features disclosed herein can be used in any combination or configuration, and is not limited to the particular combinations or configurations expressly specified or illustrated herein. Thus, in some embodiments, one or more of the features disclosed herein may be used without one or more other feature disclosed herein. In some embodiments, each of the features disclosed herein may be used without any one or more of the other features disclosed herein. In some embodiments, one or more of the features disclosed herein may be used in combination with one or more other features that is/are disclosed (herein) independently of said one or more of the features. In some embodiments, each of the features disclosed (herein) may be used in combination with any one or more other feature that is disclosed herein.

Unless stated otherwise, a locking mechanism is not limited to two lips that engage one another. In some embodiments, a locking mechanism may comprise any type of catch and/or other structures (cooperating or otherwise) that define an interference to prevent release and/or other relative movement.

Unless stated otherwise, terms such as, for example, "piece" and "member" may each be a single integral part or an assembly of multiple parts.

Unless stated otherwise, terms such as, for example, "comprises," "has," "includes," and all forms thereof, are considered open-ended, so as not to preclude additional elements and/or features.

Also unless stated otherwise, terms such as, for example, "a" and "one" are considered open-ended, and do not mean "only a" and "only one", respectively.

Also, unless stated otherwise, the phrase "a first" does not, by itself, require that there also be a "second."

Also, unless stated otherwise, terms such as, for example, "in response to" and "based on" mean "in response at least to" and "based at least on," respectively, so as not to preclude being responsive to and/or based on, more than one thing.

Also, unless stated otherwise, the phrase "A and/or B" means the following combinations: (i) A but not B, (ii) B but not A, and (iii) A and B. It should be recognized that the meaning of any phrase that includes the term "and/or" can be determined based on the above. For example, the phrase "A, B and/or C" means the following combinations: (i) A but not B and not C, (ii) B but not A and not C, (iii) C but not A and not B, (iv) A and B but not C, (v) A and C but not B, (vi) B and C but not A, and (vii) A and B and C. Further combinations using and/or shall be similarly construed.

As may be recognized by those of ordinary skill in the pertinent art based on the teachings herein, numerous changes and modifications may be made to the above-described and other embodiments of the present invention without departing from its scope as defined in the claims. For example, the components of the connector assembly may be made of any of numerous different materials that are currently known, or that later become known for performing the function(s) of each such component. Similarly, the components of the connector assembly may take any of numerous different shapes and/or configurations. In addition, the connector assembly may be used to inject any of numerous different types of fluids or other substances for any of numerous different applications, including, for example, medicaments, pharmaceuticals, vaccines, liquid nutrition products, supplements, and numerous other products that are currently known, or later become known. In addition, the characteristics of the connector assembly may be adjusted, including for example the shape and/or configuration of the penetrable septum and/or the piercing member, to meet the requirements of any of numerous different applications and/or products to be dispensed. Accordingly, this detailed description of currently preferred embodiments is to be taken in an illustrative, as opposed to a limiting sense.

What is claimed is:

1. A connector comprising:
   a first piece;
   a piercing member attached to the first piece; and
   a second piece, the piercing member being slidingly receivable within the second piece;
   wherein the piercing member and the second piece are movable relative to each other between a first position where the second piece closes a flow port and a second position where the flow port is open;
   the first piece further including a locking mechanism adapted to lockingly connect the first piece to a device when engaged therewith, thereby preventing subsequent disconnection and disengagement of the first piece and the device.

2. A connector as defined in claim 1, wherein, upon said engagement of the first piece and the device, the second piece is moved from the first position to the second position.

3. A connector as defined in claim 1, wherein the locking mechanism comprises an inward lip on the first piece.

4. A connector as defined in claim 3, wherein the inward lip is adapted to engage an outward lip on the device after the outward lip slides past the inward lip.

5. A connector as defined in claim 4, wherein the first piece comprises an inner surface and the second piece comprises a stop surface that makes contact with the inner surface to stop the piercing member from further axial movement relative to the device once the inward lip engages the outward lip.

6. A connector as defined in claim 1, wherein the connector is partially enclosed within a dispensing head.

7. A connector as defined in claim 6, wherein the dispensing head includes a one-way valve and a manually-engageable actuator.

8. A connector as defined in claim 7, wherein the connector is attachable to a squeeze tube.

9. A connector as defined in claim 1, further comprising a removable seal on the second piece.

10. A connector as defined in claim 1, wherein the locking mechanism cannot be unlocked.

11. A connector assembly comprising:
    a first piece;
    a piercing member attached to the first piece and having a flow port; and
    a second piece;
    wherein the piercing member is slidingly receivable within the second piece, wherein the piercing member and the second piece are movable relative to each other between a first position where the second piece closes the flow port and a second position where the flow port is open;
    the first piece including a locking mechanism that lockingly engages with a device when connected thereto, preventing subsequent disconnection and disengagement of first piece and the device.

12. A connector assembly as defined in claim 11 wherein upon initial connection of the first piece to the device, the second piece is moved from the first position to the second position.

13. A connector assembly as defined in claim 11, wherein the locking mechanism comprises an inward lip on the first piece.

14. A connector assembly as defined in claim 13, wherein the inward lip is adapted to engage an outward lip on the device after the outward lip slides past the inward lip.

15. A connector assembly as defined in claim 14, wherein the first piece comprises an inner surface and the second piece comprises a stop surface that makes contact with the inner surface to stop the piercing member from further axial movement relative to the device once the inward lip engages the outward lip.

16. A connector assembly as defined in claim 11, wherein the connector is partially enclosed within a dispensing head.

17. A connector assembly as defined in claim 16, wherein the dispensing head includes a one-way valve and a manually-engageable actuator.

18. A connector assembly as defined in claim 16, wherein the dispensing head is attachable to a squeeze tube.

19. A connector assembly as defined in claim 11, further comprising a removable seal on the second piece.

20. A connector assembly as defined in claim 11, wherein the locking mechanism cannot be unlocked.

21. A device comprising:
   a penetrable septum moveable between (i) a first position, wherein the penetrable septum is uncompressed, and (ii) a second position, wherein the penetrable septum is compressed; and
   a single use connector assembly including a piercing member attached to a first piece of the connector, with the piercing member slidingly receivable within a second piece of the connector, wherein one or more of the piercing member or the penetrable septum is axially moveable with respect to the other of the piercing member and the penetrable septum in an unlocked position prior to and during usage of the connector, and the one or more of the piercing member or the penetrable septum is no longer axially moveable with respect to the other of the piercing member and the penetrable septum in a locked position.

22. A device as defined in claim 21, wherein the second piece is adapted to move the septum from the first position to the second position.

23. A device as defined in claim 22, wherein the second piece is further adapted to move from an initial position relative to the first piece wherein the second piece is not engaging the septum and the septum is in the first position, to an advanced, different position relative to the first piece wherein the second piece is engaging the septum and the septum is in the second position.

24. A method comprising:
   inserting a piercing member of a connector assembly into a penetrable septum, the connector assembly further including a first piece attached to the piercing member, and a second piece, wherein the piercing member is slidingly received within the second piece; and
   locking the piercing member of the connector in the penetrable septum.

25. A method as defined in claim 24, wherein the locking step comprises fixing relative positioning of the piercing member and the penetrable septum such that neither is axially moveable with respect to the other.

26. A method as defined in claim 24 wherein the locking is permanent.

27. A method as defined in claim 24, wherein the penetrable septum is part of a device, and the method further includes starting a moving step prior to the inserting step, wherein the move step includes moving one or more of the connector assembly or the device toward each other.

* * * * *